United States Patent
Hegde et al.

(10) Patent No.: US 6,461,997 B1
(45) Date of Patent: Oct. 8, 2002

(54) TRIAZOLE SULFONES HAVING HERBICIDAL ACTIVITY

(75) Inventors: Shridhar G. Hegde, Ballwin; Martin D. Mahoney, Saint Peters, both of MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/482,501

(22) Filed: Jan. 13, 2000

Related U.S. Application Data

(60) Provisional application No. 60/116,142, filed on Jan. 14, 1999.

(51) Int. Cl.[7] ............... A01N 43/653; C07D 249/12
(52) U.S. Cl. .................... 504/273; 548/264.4
(58) Field of Search ............. 548/264.4; 504/273

(56) References Cited

U.S. PATENT DOCUMENTS

| | | | |
|---|---|---|---|
| 3,308,131 A | 3/1967 | McKusick | 260/294 |
| 3,952,001 A | 4/1976 | Brookes et al. | 260/308 |
| 4,280,831 A | 7/1981 | Patel | 71/92 |
| 4,810,271 A | 3/1989 | Nakayama et al. | 71/92 |
| 5,211,739 A | 5/1993 | Lopez | 504/273 |

FOREIGN PATENT DOCUMENTS

| | | |
|---|---|---|
| EP | 0 780 381 | 6/1997 |
| GB | 1 433 882 | 4/1976 |

OTHER PUBLICATIONS

Potts (1961) The chemistry of 1,2,4-triazoles. Chemical Reviews 61, 87–127.

Su (1994) An efficient method for the oxidation of sulfides to sulfones. Tetrahedron Letters 35, 4955–4958.

*Primary Examiner*—Patricia L. Morris
(74) *Attorney, Agent, or Firm*—Monsanto Company; Joseph A. Schaper; Ira D. Finkelstein

(57) ABSTRACT

New herbicidal compounds are provided having the formula

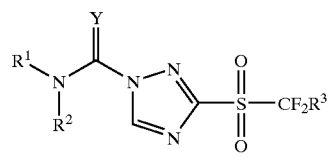

wherein Y is oxygen or sulfur; $R^1$ and $R^2$ are each independently a $C_{1-4}$ hydrocarbyl group, unsubstituted or substituted with one or more halogen, haloalkyl, hydroxy, alkoxy, carboxy, amido, cyano or amino groups; or $R^1$ and $R^2$, together with the carbamoyl nitrogen atom to which they are attached, form a nitrogen-containing five or six membered ring, the ring being optionally interrupted by an ethereal oxygen atom and unsubstituted or substituted with one or more hydroxy, amido, cyano, amino or $C_{1-8}$ alkyl, alkenyl, alkynyl, cycloalkyl, arylalkyl, alkoxy, aminoalkyl or haloalkyl groups; and $R^3$ is hydrogen, halogen, or an alkyl, cycloalkyl, alkenyl, cycloalkenyl, cycloalkylalkenyl, aryl, arylalkyl, alkylthio or arylalkylthio group that is unsubstituted or substituted with one or more halo, hydroxy, alkoxy, acetyloxy, benzoyloxy, alkoxycarbonyl, silyl or alkylsilyl groups; or an agronomically acceptable acid addition salt or metal complex of such compound.

7 Claims, No Drawings

TRIAZOLE SULFONES HAVING HERBICIDAL ACTIVITY

This Application claims the benefit of U.S. provisional application Ser. No. 60/116,142 filed Jan. 14, 1999.

FIELD OF THE INVENTION

The present invention relates to herbicidal compounds useful in agriculture and related industries. More specifically, the present invention relates to a new class of compounds effective as selective herbicides, to compositions comprising such compounds, and to methods of controlling weeds with such compounds and compositions thereof.

BACKGROUND OF THE INVENTION

Triazole derivatives have, for many years, been investigated for a wide range of utilities. For example, Potts, Chemical Reviews, 61, 87–127 (1961) is cited in U.S. Pat. No. 3,308,131 as showing that various 1,2,4-triazole compounds have found commercial application as herbicides, defoliants, photographic reagents, rubber chemicals and in polymers. U.S. Pat. No. 3,308,131 itself discloses 1,2,4-triazole compounds having a di-aliphatically substituted tertiary carbamoyl group attached to a nitrogen atom of the triazole nucleus, and in which the carbon atoms of the triazole nucleus are bonded to hydrogen, halogen, carbon or sulfur atoms. These triazoles are disclosed to be particularly useful as insecticides.

Other 1,2,4-triazoles have been disclosed as having utility as herbicides. For example, U.S. Pat. No. 5,211,739 discloses herbicidal 1-(disubstituted carbamoyl or thiocarbamoyl)-1,2,4-triazol-3-yl sulfonates and thiosulfonates. U.S. Pat. No. 3,952,001 discloses herbicidal 1-carbamoyl-1,2,4-triazoles having haloalkylsulfinyl or haloalkylsulfonyl substituents but teaches that the "haloalkyl radical" is preferably "attached to a carbon atom other than that which is attached to the ... sulphur atom of the group" defined as the haloalkylsulfinyl or haloalkylsulfonyl moiety. U.S. Pat. No. 4,810,271 discloses herbicidal 1-(disubstituted carbamoyl or thiocarbamoyl)-1,2,4-triazol-3-yl cycloalkyl(lower)alkyl, oxacycloalkyl(lower)alkyl or dioxacycloalkyl(lower)alkyl sulfonates and thiosulfonates. U.S. Pat. No. 4,280,831 discloses one herbicidal compound which is 3-benzylsulfonyl-1-diethylcarbamoyl-1,2,4-triazole.

SUMMARY OF THE INVENTION

The present invention provides a compound of formula (I)

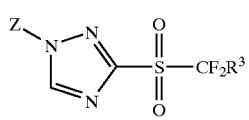

(I)

wherein $R^3$ is hydrogen, halogen or a group having a molecular weight of 15 to about 500, having up to 34 carbon atoms and comprising a hydrocarbyl moiety that is unsubstituted or substituted with one or more heteroatom-containing groups wherein heteroatoms are selected from oxygen, sulfur, nitrogen, halogen and silicon, and Z is a carbamoyl or thiocarbamoyl group having directly attached to the nitrogen atom thereof, each by a carbon-nitrogen bond, two substituent groups each independently comprising a $C_{1-14}$ hydrocarbyl moiety that is unsubstituted or substituted with one or more heteroatom-containing groups wherein heteroatoms are selected from oxygen, nitrogen and halogen, said substituent groups optionally being joined to form, with said nitrogen atom, a ring structure, Z having a molecular weight of 72 to about 500; or an agronomically acceptable acid addition salt or metal complex of a compound of formula (I).

More particularly, the present invention provides a compound of formula (II)

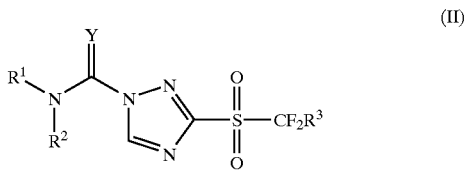

(II)

wherein:
Y is oxygen or sulfur;
$R^1$ and $R^2$
(a) are each independently a $C_{1-14}$ hydrocarbyl group, preferably a linear or branched aliphatic or alicyclic group that is saturated or has one or more olefinic and/or acetylenic bonds, and is unsubstituted or substituted with one or more halogen, haloalkyl, hydroxy, alkoxy, carboxy, amido, cyano or amino groups, wherein amido and amino groups are each unsubstituted or further substituted with one or two hydrocarbyl groups; or
(b) together with the carbamoyl nitrogen atom to which they are attached, form a nitrogen-containing five or six membered ring, the ring being optionally interrupted by an ethereal oxygen atom and unsubstituted or substituted with one or more hydroxy, amido, cyano, amino or $C_{1-8}$ alkyl, alkenyl, alkynyl, cycloalkyl, arylalkyl, alkoxy, aminoalkyl or haloalkyl groups, wherein amido and amino groups are each unsubstituted or further substituted with one or two hydrocarbyl groups;

$R^1$ and $R^2$, together with the carbamoyl or thiocarbamoyl group to which they are attached, having a total molecular weight of 72 to about 500; and $R^3$ is hydrogen, halogen, or an alkyl, cycloalkyl, alkenyl, cycloalkenyl, cycloalkylalkenyl, aryl, arylalkyl, alkylthio or arylalkylthio group that is unsubstituted or substituted with one or more halo, hydroxy, alkoxy, acetyloxy, benzoyloxy, alkoxycarbonyl, silyl or alkylsilyl groups, wherein aryl rings are unsubstituted or substituted with one to three substituents independently selected from alkyl, alkenyl, alkynyl, cycloalkyl, halo, haloalkyl, alkoxy, haloalkoxy, cyano, nitro, alkoxycarbonyl, alkylthio and haloalkylthio groups; $R^3$ having a molecular weight of 15 to about 500 and having 0–34 carbon atoms;

or an agronomically acceptable acid addition salt or metal complex of a compound of formula (II).

Illustratively, $R^1$ and $R^2$ can be alkyl, alkenyl, alkynyl, cycloalkyl, cycloalkenyl, alkylcycloalkyl, alkenylcycloalkyl, alkynylcycloalkyl, cycloalkylalkyl, cycloalkenylalkyl, alkylcycloalkylalkyl, alkenylcycloalkylalkyl, alkynylcycloalkylalkyl, haloalkyl, haloalkenyl, haloalkynyl, halocycloalkyl, alkoxyalkyl, alkoxyalkenyl, alkoxyalkynyl, alkoxycycloalkyl, haloalkoxyalkyl, haloalkoxyalkenyl, haloalkoxyalkynyl, haloalkoxycycloalkyl, halocycloalkylalkyl or alkoxycycloalkylalkyl groups. Alternatively, $R^1$ and $R^2$ can illustratively together form a $C_{4-5}$ alkylene group that is unsubstituted or substituted with one or two substituents independently selected from halo, hydroxy and alkoxy, alkyl, alkenyl, alkynyl, cycloalkyl, cycloalkylalkyl and cycloalkenylalkyl groups unsubstituted or further substituted with halo, hydroxy, alkoxy, alkyl, alkenyl, alkynyl, cycloalkyl, haloalkyl or haloalkoxy groups.

Illustratively, $R^3$ can be hydrogen, halogen or an alkyl, haloalkyl, cycloalkyl, halocycloalkyl, alkenyl, cycloalkylalkenyl, alkoxyalkenyl, haloalkenyl, cycloalkenyl, halocycloalkenyl, alkylthio, hydroxyalkylthio, alkoxyalkylthio, haloalkylthio, acetyloxyalkylthio, benzoyloxyalkylthio, alkoxycarbonylalkylthio group or an aryl, arylalkyl or arylalkylthio group unsubstituted or substituted as indicated above.

The present invention also provides a composition for use as a herbicide comprising a herbicidally effective amount of a compound of formula (I) or (II) as defined above or an agronomically acceptable acid addition salt or metal complex thereof. Such a composition can be a concentrate, further comprising one or more agronomically acceptable inert formulation ingredients or excipient substances, or it can be ready-to-use, further comprising an agronomically acceptable carrier.

The present invention also provides a method of using a compound of formula (I) or (II) as a herbicidal agent, comprising applying a herbicidally effective amount of such a compound to soil or plants.

DETAILED DESCRIPTION OF THE INVENTION

Preferred Substituents of Compounds of Formula (II)

In compounds of the invention as defined in formula (II) above, the following are preferred substituents.

Preferably $R^1$ and $R^2$ are independently $C_{1-6}$ alkyl, $C_{2-4}$ alkenyl, $C_{2-4}$ alkynyl, $C_{3-6}$ cycloalkyl, $C_{5-6}$ cycloalkenyl, $(C_{1-3})$alkyl$(C_{3-6})$cycloalkyl, $(C_{2-3})$alkenyl$(C_{3-6})$cycloalkyl, $(C_{2-3})$alkynyl$(C_{3-6})$cycloalkyl, halo$(C_{1-6})$alkyl, halo$(C_{2-4})$alkenyl, halo$(C_{2-4})$alkynyl, halo$(C_{3-6})$cycloalkyl, $(C_{1-4})$alkoxy$(C_{1-6})$alkyl, $(C_{1-4})$alkoxy$(C_{2-4})$alkenyl, $(C_{1-4})$alkoxy$(C_{2-4})$alkynyl), $(C_{1-4})$alkoxy$(C_{3-6})$cycloalkyl halo$(C_{1-4})$alkoxy$(C_{1-6})$alkyl, halo$(C_{1-4})$alkoxy$(C_{2-4})$alkenyl, halo$(C_{1-4})$alkoxy$(C_{2-4})$alkynyl, halo$(C_{1-4})$alkoxy$(C_{3-6})$cycloalkyl, $(C_{3-6})$cycloalkyl$(C_{1-4})$alkyl, $(C_{5-6})$cycloalkenyl$(C_{1-4})$alkyl, $(C_{1-4})$alkyl$(C_{3-6})$cycloalkyl$(C_{1-4})$alkyl, $(C_{1-4})$alkyl$(C_{5-6})$cycloalkenyl$(C_{1-4})$alkyl, $(C_{2-4})$alkenyl$(C_{3-6})$cycloalkyl$(C_{1-4})$ alkyl, $(C_{2-4})$alkynyl$(C_{5-6})$cycloalkyl$(C_{1-4})$alkyl, halo$(C_{3-6})$cycloalkyl$(C_{1-4})$alkyl or $(C_{1-4})$alkoxy$(C_{3-6})$cycloalkyl$(C_{1-4})$alkyl; or $R^1$ and $R^2$ together represent an unsubstituted $C_{4-5}$ alkylene group or a $C_{4-5}$ alkylene group substituted with one or two substituents each independently selected from the group consisting of $C_{1-4}$ alkyl, $C_{2-4}$ alkenyl, $C_{2-4}$ alkynyl, $C_{3-6}$ cycloalkyl, $C_{1-4}$ alkoxy, halo and halo$(C_{1-4})$alkoxy, so as to form a nitrogen-containing five or six membered ring together with the carbamoyl nitrogen atom to which they are attached.

Preferably $R^3$ is a hydrogen, halogen, $C_{1-8}$ alkyl, halo$(C_{1-4})$alkyl, $C_{3-6}$ cycloalkyl, halo$(C_{3-6})$cycloalkyl, $C_{2-4}$ alkenyl, $(C_{3-6})$cycloalkyl$(C_{2-4})$alkenyl, $(C_{1-4})$alkoxy$(C_{2-4})$ alkenyl, halo$(C_{2-4})$alkenyl, $C_{3-6}$ cycloalkenyl, halo$(C_{3-6})$ cycloalkenyl, $C_{6-10}$ aryl or $(C_{6-10})$aryl$(C_{1-6})$alkyl group, wherein $C_{6-10}$ aryl or $(C_{6-10})$aryl$(C_{1-6})$alkyl groups are unsubstituted or substituted on the aryl ring with one to three substituents each independently selected from $C_{1-6}$ alkyl, $C_{2-4}$ alkenyl, $C_{2-4}$ alkynyl, $C_{3-6}$ cycloalkyl, halo, halo$(C_{1-4})$ alkyl, $C_{1-4}$ alkoxy, halo$(C_{1-4})$alkoxy, cyano, nitro, $(C_{1-6})$ alkoxycarbonyl, $(C_{1-4})$alkylthio and halo$(C_{1-4})$alkylthio groups.

The term "alkyl" in the present specification includes straight and branched chain alkyl groups, for example $C_{1-6}$ alkyl groups such as methyl, ethyl, n-propyl, isopropyl, n-butyl, isobutyl, sec-butyl, n-pentyl, isopentyl and n-hexyl groups. The term "alkenyl" includes, for example, $C_{2-4}$ alkenyl groups such as vinyl, allyl, methallyl and 2-butenyl groups. The term "alkynyl" includes, for example, $C_{2-4}$ alkynyl groups such as a propargyl group.

The term "halo" includes fluoro, chloro, bromo and iodo. The term "alkoxy" includes, for example, methoxy, ethoxy, n-propoxy, isopropoxy, n-butoxy and isobutoxy groups. Illustrative alkoxyalkyl groups include 2-methoxyethyl, 2-ethoxyethyl, 2-propoxyethyl, 2-n-butoxyethyl, 3-methoxypropyl, 3-ethoxypropyl, 2-methoxypropyl and 2-ethoxypropyl groups. Haloalkyl groups include, for example, fluoromethyl, difluoromethyl, chlorodifluoromethyl, bromodifluoromethyl, 2-chloroethyl, 2-bromoethyl, 2-fluoroethyl, 3-chloropropyl, 3-bromopropyl, 4-chlorobutyl, 4-bromobutyl and 5-chloropentyl.

Illustrative $C_{2-4}$ cycloalkyl groups are cyclopropyl, cyclopentyl and cyclohexyl groups. An illustrative $(C_{3-6})$ cycloalkyl$(C_{2-4})$alkenyl group is a 1-cyclohexyl-1-propen-3-yl group. An illustrative $(C_{2-4})$alkoxy$(C_{2-4})$alkenyl group is a 4-ethoxy-2-buten-1-yl group. Illustrative $C_{5-6}$ cycloalkenyl groups are 1-cyclopenten-1-yl and 2-cyclohexen-1-yl groups. An illustrative $(C_{2-3})$alkenyl$(C_{3-6})$cycloalkyl group is a 1-cyclohexylethen-2-yl group. An illustrative $(C_{2-3})$ alkynyl$(C_{3-6})$cycloalkyl group is a propargylcyclohexyl group.

The term "aryl" as used in the present specification means an aromatic ring structure having, for example, 6–10 carbon atoms, preferably a phenyl or naphthyl group. Typical aryl and substituted aryl groups in compounds encompassed by this invention are phenyl, naphthyl, 2-chlorophenyl, 3-chlorophenyl, 4-chlorophenyl, 4-bromophenyl, 4-fluorophenyl, 2,3-dichlorophenyl, 2,3-difluorophenyl, 2,4-dichlorophenyl, 2-methylphenyl, 3-methylphenyl, 4-methylphenyl, 2,4-dimethylphenyl, 2-chloro-6-methylphenyl, 2-methoxy-3-methylphenyl, 3-methoxy-2-methylphenyl, 3-(trifluoromethyl)phenyl, 4-(trifluoromethyl)phenyl, 2-(difluoromethoxy)phenyl, 4-cyanophenyl, 4-nitrophenyl, 4-methoxyphenyl, 4-(methylthio)phenyl, 4-isopropylphenyl, 2,4,6-trichlorophenyl, 4-iodophenyl, 4-fluoro-2-methylphenyl, 4-chloro-2-methylphenyl, 2-(fluoromethyl)phenyl, 4-(2-chloroethyl)phenyl, 4-t-butylphenyl, 4-t-butoxyphenyl, 2,4-dicyanophenyl, 4-allylphenyl, 4-propargylphenyl, 4-cyclopropylphenyl, 4-cyclohexylphenyl, 4-(chloromethylthio)phenyl, 2-(chloromethoxy)phenyl, 4-(methoxycarbonyl)phenyl and 3-isobutylphenyl.

The term "arylalkyl" as used in the present specification means an alkyl group substituted with an aryl group, for example a $(C_{6-10})$aryl$(C_{1-6})$ alkyl group such as a 1-(naphthyl)methyl, 2-(4-chlorophenyl)ethyl or 6-(2,4-difluorophenyl)hexyl group.

This invention also provides acid addition salts of a compound of formula (II) wherein one or more of the protonatable nitrogen atoms of the compound are protonated and the acid is selected to give an anionic counterion in such a manner that the sum of the valence charges of the protonated compound and the anion equals zero.

This invention further provides metal salt complexes of a compound of formula (II) wherein the salt comprises a cation of a metal selected from Groups IIA, IVA, IB, IIB, VIB, VIIB and VIII of the Periodic Table and an anionic counterion such that the sum of the valence charges of the cation and anion equals zero.

Preparation of Compounds of Formula (II)

A 1-(disubstituted carbamoyl or thiocarbamoyl)-1,2,4-triazole compound of formula (II) can be generally produced by the hereinafter described process.

In such a process, described in Equation 1, a triazole compound having the general formula (III) is reacted with a carbamoyl or thiocarbamoyl halide of the general formula (IV). In formulas (III) and (IV), $R^1$, $R^2$, $R^3$ and Y are as defined for Formula (II) and A is chlorine, bromine or fluorine, preferably chlorine.

Equation 1

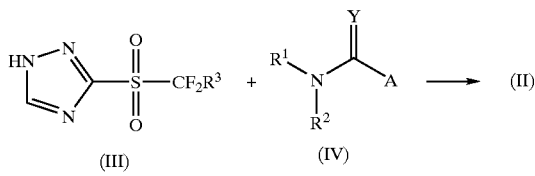

The reaction is suitably effected in a solvent in the presence of an acid acceptor. The equivalent ratio of the triazole compound (III), the carbamoyl or thiocarbamoyl halide (IV) and the acid acceptor is usefully 1:1–1.5:1–10. Examples of suitable solvents are aromatic hydrocarbons (e.g., benzene, toluene, xylene), halogenated hydrocarbons (e.g., chloroform, dichloromethane, chlorobenzene), ethers (e.g., diethyl ether, tetrahydrofuran), ketones (e.g., acetone, 2-butanone), organic bases (e.g., pyridine, triethylamine, N,N-diethylaniline), acetonitrile, N,N-dimethylformamide, dimethylsulfoxide and water. As the acid acceptor, there can be used inorganic bases (e.g., sodium hydroxide, potassium hydroxide, sodium carbonate, potassium carbonate, sodium hydrogen carbonate), organic bases (e.g., pyridine, triethylamine, N,N-diethylaniline), etc. The reaction can normally be carried out at a temperature between the freezing point and the boiling point of the solvent, preferably from 0° C. to 150° C., within a period of 10 minutes to 48 hours. In an alternative procedure, the triazole compound (III) can be converted to an alkali metal (e.g., sodium, potassium) salt thereof by reacting with an alkali metal hydride, amide or alkoxide in accordance with known methods prior to the reaction with the carbamoyl or thiocarbamoyl halide (IV).

The carbamoyl or thiocarbamoyl halide of formula (IV) can be prepared by reacting a secondary amine of formula $HNR^1R^2$, in which $R^1$ and $R^2$ are as defined above for formula (II), with a carbonyl or thiocarbonyl halide $CYA_2$ where A and Y are as defined above for formula (IV), in accordance with known methods.

The triazole compound of formula (III) can be prepared by a process, described in Equation 2, in which a 1-(N,N-diethylcarbamoyl)triazole of formula (V) wherein $R^3$ is as defined above for formula (II) is reacted with a sodium alkoxide (NaOR) in which R is methyl, ethyl, propyl, isopropyl or butyl, the reaction taking place in the corresponding alkanol (ROH) solvent. The sodium salt of the compound of formula (III) thus produced is acidified with dilute mineral acid and extracted with a solvent such as a halogenated hydrocarbon (e.g., chloroform, dichloromethane), ether (e.g., diethyl ether) or ester (e.g., ethyl acetate).

Equation 2

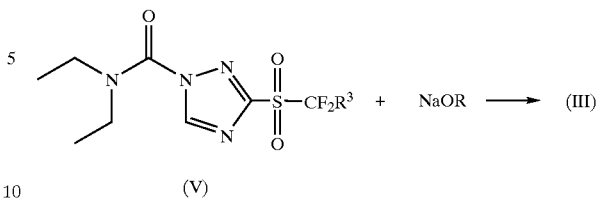

The reaction can normally be carried out at a temperature between the freezing point and the boiling point of the solvent, preferably from 0° C. to 150° C., within a period of 10 minutes to 48 hours.

The 1-(N,N-diethylcarbamoyl)triazole of formula (V) can be prepared by a number of routes including the following:

(a) A compound of formula (V) in which $R^3$ is hydrogen, halogen or a haloalkyl, aryl, arylcarbonyl or alkoxycarbonyl group can be prepared by oxidation of a triazole sulfide of formula (VI)

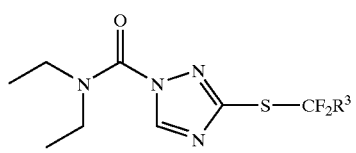

in accordance with a method described by W. Su, Tetrahedron Letters, 1994, volume 35, pages 4955–4958.

Thus, in a typical reaction, a compound of formula (VI) is stirred with sodium periodate and a catalytic amount of ruthenium trichloride hydrate in a mixture of carbon tetrachloride, acetonitrile and water. The equivalent ratio of triazole sulfide (VI), sodium periodate and ruthenium trichloride hydrate is usefully 1:3–5:0.05. The reaction can normally be carried out at room temperature within a period of 30 minutes to 48 hours, more typically 8–24 hours.

The triazole sulfide of formula (VI) in which $R^3$ is hydrogen can be prepared from the corresponding compound in which $R^3$ is a bromo group by reaction with a reducing agent such as a mixture of ammonium formate and ammonium persulfate in a solvent such as N,N-dimethylformamide.

A triazole sulfide of formula (VI) in which $R^3$ is halo, haloalkyl, aryl, arylcarbonyl or alkoxycarbonyl can be prepared by a process described in Equation 3 in which the 3,3'-(dithiobis)-1,2,4-triazole compound of formula (VII) is reacted with a halide compound of the formula (VIII) in which G is a bromo or iodo group.

Equation 3

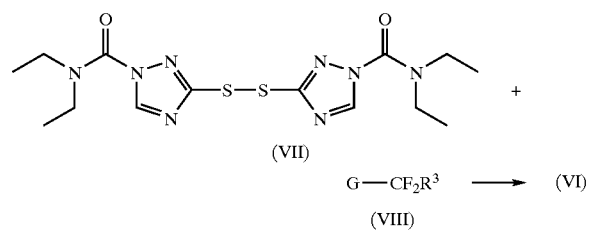

The reaction is suitably effected in a mixture of N,N-dimethylformamide and water in the presence of sodium dithionite and disodium hydrogen phosphate. The equivalent ratio of 3,3'-(dithiobis)-1,2,4-triazole compound (VII), halide compound (VIII), sodium dithionite and disodium hydrogen phosphate is usefully 1:1.5–6:1.5:1.5. The reaction can normally be carried out at a temperature between −78° C. and 40° C. preferably from 0° C. to 25° C., within a period of 1 hour to 48 hours.

The 3,3'-(dithiobis)-1,2,4-triazole compound (VII) can be prepared by a process of reacting 3,3'-(dithiobis)-1,2,4-triazole, a compound previously described in French Patent No. 2,592,381, with N,N-diethylcarbamoyl chloride in the presence of an acid acceptor such as pyridine.

(b) Compounds of formula (V) in which $R^3$ is a group —S—$R^4$ group wherein $R^4$ is an alkyl, arylalkyl, alkoxycarbonylalkyl, hydroxyalkyl or alkoxyalkyl group can be prepared by a process described in Equation 4 in which 3-(bromodifluoromethylsulfonyl)-1-(N,N-diethylcarbamoyl)-1,2,4-triazole (IX), prepared as described above, is reacted with a disulfide compound of formula (X).

Equation 4

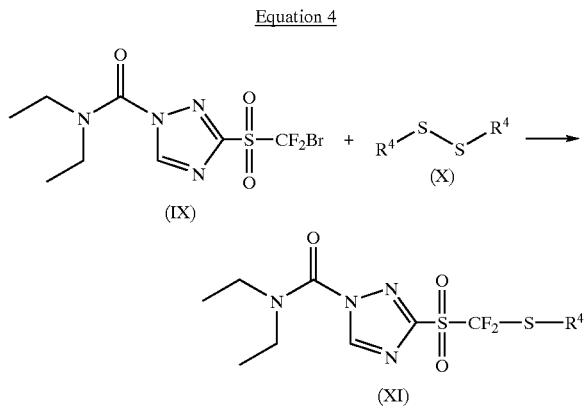

The reaction is suitably effected in a mixture of N,N-dimethylformamide and water in the presence of sodium dithionite and disodium hydrogen phosphate. The equivalent ratio of compound (IX), disulfide compound (X), sodium dithionite and disodium hydrogen phosphate is usefully 1:2:1.5:1.5. The reaction can normally be carried out at a temperature between −78° C. and 40° C., preferably from 0° C. to 25° C., within a period of 1 hour to 24 hours.

(c) Compounds of formula (V) in which $R^3$ is a group —S—$R^4$ group wherein $R^4$ is an alkylcarbonyloxyalkyl or arylcarbonyloxyalkyl group can be prepared from the corresponding compounds in which $R^4$ is a hydroxyalkyl group by reaction with an alkylcarbonyl chloride or an arylcarbonyl chloride in the presence of an acid acceptor such as pyridine or triethylamine.

(d) Compounds of formula (V) in which $R^3$ is a —$CH_2$—C($R^5$)=$CH_2$ group wherein $R^5$ is hydrogen, halogen or an alkyl or trialkylsilylalkyl group can be prepared by a process described in Equation 5 in which 3-(bromodifluoromethylsulfonyl)-1-(N,N-diethylcarbamoyl)-1,2,4-triazole (IX) is reacted with a 2-(2-alkenylthio)-2-thiazoline compound of formula (XII).

Equation 5

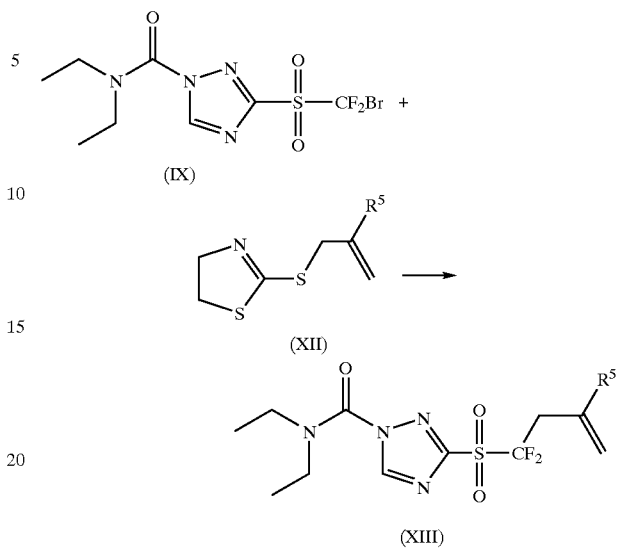

The reaction is suitably effected in a mixture of N,N-dimethylformamide and water in the presence of sodium dithionite and disodium hydrogen phosphate. The equivalent ratio of compound (IX), 2-(2-alkenylthio)-2-thiazoline compound (XII), sodium dithionite and disodium hydrogen phosphate is usefully 1:2:1.5:1.5. The reaction can normally be carried out at a temperature between −78° C. and 40° C., preferably from 0° C. to 25° C., within a period of 1 hour to 24 hours.

The following Examples 1–94 describe specific working embodiments for the preparation of representative compounds according to this invention.

EXAMPLE 1

Preparation of 3-(bromodifluoromethylsulfonyl)-1-(N,N-diethylcarbamoyl)-1,2,4-triazole (a) Preparation of 3,3'-(dithiobis)-1,2,4-triazole To a mechanically stirred slurry of 101 g (1 mol) 3-mercapto-1,2,4-triazole in 500 ml dichloromethane was added 79 g (81 ml, 1 mol) dry pyridine. The resulting mixture was cooled in an ice bath and 88 g (63.6 ml, 0.5 mol) benzenesulfonyl chloride was added dropwise over a period of 1 h. The ice bath was removed and the mixture was stirred for 16 h at room temperature. Dichloromethane was then evaporated and the resulting residue was mechanically stirred with a mixture of 500 ml water and 300 ml ethyl acetate for 1 h. The mixture was filtered to isolate the resulting precipitate, which was then washed with 200 ml water and then 200 ml ethyl acetate. Drying the precipitate under vacuum (1 mm Hg) at 60–70° C. gave 92 g (92% yield) of the desired 3,3'-(dithiobis)-1,2,4-triazole as a white solid.

(b) Preparation of 3,3'-(dithiobis)-1-(N,N-diethylcarbamoyl)-1,2,4-triazole

To a mechanically stirred slurry of 92 g (0.46 mol) 3,3'-(dithiobis)-1,2,4-triazole, prepared as above, in 400 ml dry pyridine at 0° C. was added 148.5 g (139 ml, 1.1 mol) diethylcarbamoyl chloride dropwise over a period of 1 h. The resulting mixture was stirred for 20 h at room temperature, and then slowly added to 600 ml cold 4N hydrochloric acid solution. The mixture was stirred for 1 h and extracted with ethyl acetate (3×300 ml). The combined resulting organic layers were washed with water, dried over MgSO$_4$ and evaporated. The resulting oily residue was stirred with 500 ml hexane to give a pale yellow solid. The precipitate was filtered, washed with hexane and air-dried to give 165 g (90% yield) of the desired 3,3'-(dithiobis)-1-(N, N-diethylcarbamoyl)-1,2,4-triazole.

(c) Preparation of 3-(bromodifluoromethylthio)-1-(N,N-diethylcarbamoyl)-1,2,4-triazole To a mechanically stirred slurry of 23.5 g (0.135 mol) sodium dithionite and 19.2 g (0.135 mol) disodium hydrogen phosphate (sodium phosphate, dibasic) in 80 ml N,N-dimethylformamide at 0° C. was added 80 ml water, followed by 36 g (0.09 mol) 3,3'-(dithiobis)-1-(N,N-diethylcarbamoyl)-1,2,4-triazole, prepared as above. While stirring vigorously at 0° C., 40 ml dibromodifluoromethane was added in four 10 ml portions at 30 min intervals. The reaction was then stirred for 20 h with slow warming to room temperature. The mixture was then diluted with 400 ml water and extracted with ether (3×200 ml). The combined resulting organic layers were washed with ether, dried over MgSO$_4$ and evaporated. Preparative LC purification of the residue using 20% ethyl acetate-hexane gave 27 g (46% yield) of the desired 3-(bromodifluoromethylthio)-1-(N,N-diethylcarbamoyl)-1,2,4-triazole as a colorless oil which solidified upon storing in a refrigerator.

(d) Preparation of 3-(bromodifluoromethylsulfonyl)-1-(N,N-diethylcarbamoyl)-1,2,4-triazole To a solution of 57 g (0.17 mol) 3-(bromodifluoromethylthio)-1-(N,N-diethylcarbamoyl)-1,2,4-triazole, prepared as above, in 100 ml acetonitrile were sequentially added 100 ml carbon tetrachloride, 200 ml water and 11 1.23 g (0.52 mol) sodium periodate. To the resulting suspension was added 20 mg (ca 5 mol %) ruthenium trichloride hydrate and the suspension was then stirred at room temperature for 24 h. The reaction mixture was then diluted with 500 ml water, extracted with dichloromethane (3×200 ml) and the combined resulting organic layers were sequentially washed with water, saturated sodium bicarbonate solution and brine. The dichloromethane solution was dried over MgSO$_4$ and evaporated. Preparative LC purification of the residue with 40% ethyl acetate-hexane gave 53.31 g (85% yield) of the desired 3-(bromodifluoromethylsulfonyl)-1-(N,N-diethylcarbamoyl)-1,2,4-triazole as a white solid with melting point 74–75° C.

EXAMPLES 2–7

The following Examples 2–7 as shown in Table 1 were prepared in a similar manner, except that in step (c), dibromodifluoromethane was replaced by a compound of formula CF$_2$Br—R$^3$ where R$^3$ is as indicated in Table 1.

TABLE 1

| Example no. | R$^3$ | Physical constant |
|---|---|---|
| 2 | F | M.P. 52–54° C. |
| 3 | Cl | M.P. 69–71° C. |
| 4 | CF$_2$Br | M.P. 55–57° C. |
| 5 | C$_6$H$_5$ | M.P. 109–112° C. |
| 6 | C(O)C$_6$H$_5$ | M.P. 92–93° C. |
| 7 | COOCH$_2$CH$_3$ | $n_D^{25}$ = 1.4774 |

EXAMPLE 8

Preparation of 1-(N,N-diethylcarbamoyl)-3-[difluoro(ethylthio)methylsulfonyl]-1,2,4-triazole To a stirred solution of 10 g (0.028 mol) 3-(bromodifluoromethylsulfonyl)-1-(N,N-diethylcarbamoyl)-1,2,4-triazole (as prepared in Example 1) and 6.81 ml (0.055 mol) diethyl disulfide in a mixture of 30 ml N,N-dimethylformamide and 20 ml water at 0° C. was added 5.9 g (0.042 mol) sodium hydrogen phosphate and 7.23 g (0.042 mol) sodium dithionite. After 2 h, the reaction mixture was diluted with 100 ml water and extracted with ethyl acetate (3×100 ml). The combined resulting organic layers were washed with saturated sodium chloride solution, dried over MgSO$_4$ and evaporated. Preparative LC purification of the residue with 40% ethyl acetate-hexane gave 5.45 g (57% yield) of the desired 1-(N,N-diethylcarbamoyl)-3-[difluoro(ethylthio)methylsulfonyl]-1,2,4-triazole as a colorless oil having $$n_D^{25} = 1.5063.$$

EXAMPLES 9–14

Examples 9–13 as shown in Table 2 were prepared in a similar manner, except that diethyl disulfide was replaced by a compound of formula R$^4$—S—S—R$^4$ where S—R$^4$ takes the place of R$^3$ as indicated in Table 2. Example 14 was prepared in a similar way to Example 9 except that in place of the compound of Example 1, the compound of Example 4 was used as the starting material.

TABLE 2

| Example no. | R$^3$ | Physical constant |
|---|---|---|
| 9 | S—CH$_3$ | $n_D^{25}$ = 1.4975 |
| 10 | S—CH$_2$C$_6$H$_5$ | $n_D^{25}$ = 1.5465 |
| 11 | S—CH$_2$COOCH$_3$ | M.P. 56–57° C. |
| 12 | S—CH$_2$CH$_2$OH | $n_D^{25}$ = 1.5537 |
| 13 | S—CH$_2$CH$_2$OCH$_3$ | $n_D^{25}$ = 1.5058 |
| 14 | CF$_2$—S—CH$_3$ | M.P. 47–49° C. |

EXAMPLE 15

Preparation of 1-(N,N-diethylcarbamoyl)-3-(difluoromethylsulfonyl)-1,2,4-triazole (a) Preparation of 1-(N,N-diethylcarbamoyl)-3-(difluoromethylthio)-1,2,4-triazole To a stirred solution of 10.7 g (0.033 mol) 3-(bromodifluoromethylthio)-1-(N,N-diethylcarbamoyl)-1,2,4-triazole, prepared as in Example 1, step (c), in 25 ml N,N-dimethylformamide, was added 4.11 g (0.065 mol) ammonium formate and 2.24 g (0.01 mol) ammonium persulfate and the mixture was heated at 50° C. for 2.5 h. The reaction mixture was then diluted with 100 ml water and extracted with ether (3×100 ml). The combined resulting organic layers were washed with water, dried over $MgSO_4$ and evaporated to give 7.2 g (88% yield) of the desired 1-(N,N-diethylcarbamoyl)-3-(difluoromethylthio)-1,2,4-triazole as a colorless oil.

(b) Preparation of 1-(N,N-diethylcarbamoyl)-3-(difluoromethylsulfonyl)-1,2,4-triazole To a solution of 3.88 g (0.0155 mol) 1-(N,N-diethylcarbamoyl)-3-(difluoromethylthio)-1,2,4-triazole, prepared as above, in 20 ml acetonitrile were sequentially added 20 ml carbon tetrachloride, 40 ml water and 10 g (0.047 mol) sodium periodate. To the resulting suspension was added 2 mg (ca 5 mol %) ruthenium trichloride hydrate and the suspension was then stirred at room temperature for 24 h. The reaction mixture was then diluted with 100 ml water, extracted with dichloromethane (3×100 ml) and the combined resulting organic layers were sequentially washed with water, saturated sodium bicarbonate solution and brine. The dichloromethane solution was dried over $MgSO_4$ and evaporated. Preparative LC purification of the residue with 40% ethyl acetate-hexane gave 3.4 g (78% yield) of the desired 1-(N,N-diethylcarbamoyl)-3-(difluoromethylsulfonyl)-1,2,4-triazole as a white solid with a melting point of 58–59° C.

EXAMPLE 16

Example 16 ($R^3=CF_2H$) was prepared in a similar manner, using as starting material 3-(2-bromotetrafluoroethylthio)-1-(N,N-diethylcarbamoyl)-1,2,4-triazole. The resulting compound had a melting point of 42–44° C.

EXAMPLE 17

Preparation of 1-(N,N-diethylcarbamoyl)-3-[(1,1-difluoro-3-butenyl)sulfonyl]-1,2,4-triazole To a stirred solution of 10 g (0.028 mol) 3-(bromodifluoromethylsulfonyl)-1-(N,N-diethylcarbamoyl)-1,2,4-triazole, prepared as in Example 1, and 8.81 g (0.055 mol) 2-(2-propenylthio)-2-thiazoline in a mixture of 30 ml dimethylformamide and 20 ml water at 0° C., was added 5.9 g (0.042 mol) sodium hydrogen phosphate and 7.23 g (0.042 mol) sodium dithionite. After 2 h, the reaction mixture was diluted with 100 ml water and extracted with ethyl acetate (3×100 ml). The combined resulting organic layers were washed with saturated sodium chloride solution, dried over $MgSO_4$ and evaporated. Preparative LC purification of the residue with 40% ethyl acetate-hexane gave 2.59 g (29% yield) of the desired product as a colorless oil having $$n_D^{25} = 1.4896.$$

EXAMPLES 18–20

The following Examples 18–20 as shown in Table 3 were prepared in a similar manner, except that 2-(2-propenylthio)-2-thiazoline was replaced by a compound of formula

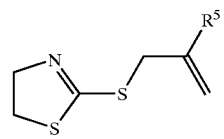

where $R^5$ is as indicated in Table 3.

TABLE 3

| Example no. | $R^5$ | Physical constant |
|---|---|---|
| 18 | $CH_3$ | $n_D^{25} = 1.4916$ |
| 19 | Br | $n_D^{25} = 1.5136$ |
| 20 | $CH_2Si(CH_3)_3$ | $n_D^{25} = 1.4890$ |

EXAMPLE 21

Preparation of 3-[(2-acetyloxyethylthio) difluoromethylsulfonyl)]-1-(N,N-diethylcarbamoyl)-1,2,4-triazole To a solution of 1.07 g (0.003 mol) 1-(N,N-diethylcarbamoyl)-3-[(2-hydroxyethylthio) difluoromethylsulfonyl]-1,2,4-triazole, prepared as in Example 12, in 10 ml dichloromethane was added 0.5 ml dry pyridine and 0.4 g (0.005 mol) acetyl chloride and the mixture was stirred at room temperature overnight. The reaction mixture was then sequentially washed with water, 5% hydrochloric acid solution and saturated sodium chloride solution. The resulting organic layer was dried over $MgSO_4$ and evaporated, and the residue was purified by flash chromatography (silica gel, 40% ethyl acetate-hexane) to give 1.06 g (88% yield) of the desired 3-[(2-acetyloxyethylthio) difluoromethylsulfonyl)]-1-(N,N-diethylcarbamoyl)-1,2,4-triazole as a colorless oil having $$n_D^{25} = 1.5237.$$

EXAMPLE 22

Example 22, 3-[(2-benzoyloxyethylthio) difluoromethylsulfonyl)]-1-(N,N-diethylcarbamoyl)-1,2,4-triazole, in which $R^3$ is $—S—CH_2CH_2OC(O)C_6H_5$, was prepared in a similar manner, except that benzoyl chloride was used in place of acetyl chloride. The compound of Example 22 had $$n_D^{25} = 1.4908.$$

EXAMPLE 23

Preparation of 3-(bromodifluoromethylsulfonyl)-1-(pyrrolidinocarbonyl)-1,2,4-triazole (a) Preparation of 3-(bromodifluoromethylsulfonyl)-1,2,4-triazole To a solution of 7 g (0.019 mol) 3-(bromodifluoromethylsulfonyl)-1-(N,N-diethylcarbamoyl)-1,2,4-triazole, prepared as in Example 1, in 50 ml methanol at room temperature was added 6.7 ml (0.029 mol) of a 25% w/v solution of sodium methoxide in methanol and the mixture was stirred for 2 h. The reaction mixture was then evaporated and the residue was triturated with ether. The resulting solid was collected by filtration, washed with ether and air-dried. A solution of the above solid in 50 ml water was acidified with concentrated hydrochloric acid and the mixture was extracted with ethyl acetate. The resulting organic layer was washed with saturated sodium chloride solution, dried over MgSO₄ and evaporated to give 3.08 g (61% yield) of the desired 3-(bromodifluoromethylsulfonyl)-1,2,4-triazole as a white solid with a melting point of 176–177° C.

(b) Preparation of 3-(bromodifluoromethylsulfonyl)-1-(pyrrolidinocarbonyl)-1,2,4-triazole To a solution of 0.12 g (0.45 mmol) 3-(bromodifluoromethylsulfonyl)-1,2,4-triazole, prepared as above, in 0.5 ml dry pyridine was added 0.07 g (0.54 mmol) pyrrolidine-1-carbonyl chloride and the mixture was agitated for 16 h at room temperature. The reaction mixture was then diluted with water and extracted with ether. The resulting organic layer was washed successively with dilute hydrochloric acid, water and saturated sodium bicarbonate solution, dried over MgSO₄ and evaporated to give 0.1 g (65% yield) of the desired 3-(bromodifluoromethylsulfonyl)-1-(pyrrolidinocarbonyl)-1,2,4-triazole as a pale yellow oil: $^1$H NMR (CDCl₃) δ(ppm) 9.1 (1H), 4.0 (2H), 3.7 (2H), 2.1 (4H).

EXAMPLES 24–94

The following Examples 24–94 shown in Table 4 were prepared in a similar manner, except that pyrrolidine-1-carbonyl chloride was replaced by a compound of formula

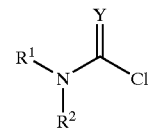

where Y, R¹ and R² are as indicated in Table 4, and the compound of Example 1 used as the starting material was replaced as necessary by compounds of other Examples described above having R³ as indicated in Table 4.

TABLE 4

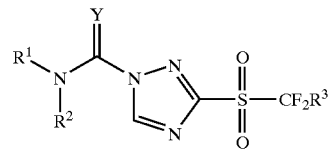

| Example no. | Y | R¹ | R² | R³ | $^1$H NMR (CDCl₃)δ (ppm) |
|---|---|---|---|---|---|
| 24 | O | —CH₂CH₂CH₂CH₂— | | H | n.d. |
| 25 | O | —CH₂CH₂OCH₂CH₂— | | H | n.d. |
| 26 | O | CH₃ | CH₃ | H | n.d. |
| 27 | O | C₆H₅ | CH₃ | H | n.d. |
| 28 | O | CH₂CH₂CH₃ | CH₂CH₃ | H | n.d. |
| 29 | O | CH₂CH₂OCH₃ | CH₃ | H | n.d. |
| 30 | O | CH₂CH=CH₂ | CH₃ | H | 8.97(1H), 6.43(1H), 5.87(1H), 5.3(2H), 4.1–4.2(2H), 3.15–3.26(3H) |
| 31 | O | CH₂C≡CH | CH₃ | H | n.d. |
| 32 | O | cyclohexyl | CH₃ | H | n.d. |
| 33 | O | CH₂C₆H₅ | CH₃ | H | n.d. |
| 34 | O | OCH₃ | CH₃ | H | n.d. |
| 35 | S | CH₂CH₃ | CH₂CH₃ | H | n.d. |
| 36 | O | —CH₂CH₂OCH₂CH₂— | | Br | n.d. |
| 37 | O | CH₃ | CH₃ | Br | n.d. |
| 38 | O | C₆H₅ | CH₃ | Br | n.d. |
| 39 | O | CH₂CH₂CH₃ | CH₂CH₃ | Br | n.d. |
| 40 | O | CH₂CH₂OCH₃ | CH₃ | Br | n.d. |
| 41 | O | CH₂CH=CH₂ | CH₃ | Br | n.d. |
| 42 | O | CH₂C≡CH | CH₃ | Br | n.d. |
| 43 | O | cyclohexyl | CH₃ | Br | n.d. |
| 44 | O | CH₂C₆H₅ | CH₃ | Br | n.d. |
| 45 | O | OCH₃ | CH₃ | Br | n.d. |
| 46 | S | CH₂CH₃ | CH₂CH₃ | Br | n.d. |
| 47 | O | —CH₂CH₂CH₂CH₂— | | SCH₂CH₃ | n.d. |
| 48 | O | —CH₂CH₂OCH₂CH₂— | | SCH₂CH₃ | 8.95(1H), 3.92(2H), 3.78(6H), 3.12(2H), 1.37(3H) |

TABLE 4-continued

Structure: $R^1R^2N-C(=Y)-$ [1,2,4-triazole]$-SO_2-CF_2R^3$

| Example no. | Y | $R^1$ | $R^2$ | $R^3$ | $^1$H NMR (CDCl$_3$)δ (ppm) |
|---|---|---|---|---|---|
| 49 | O | CH$_3$ | CH$_3$ | SCH$_2$CH$_3$ | n.d. |
| 50 | O | C$_6$H$_5$ | CH$_3$ | SCH$_2$CH$_3$ | 8.8(1H), 7.3(3H), 7.1(2H), 3.6(3H), 3.1(2H), 1.3(3H) |
| 51 | O | CH$_2$CH$_2$CH$_3$ | CH$_2$CH$_3$ | SCH$_2$CH$_3$ | n.d. |
| 52 | O | CH$_2$CH$_2$OCH$_3$ | CH$_3$ | SCH$_2$CH$_3$ | n.d. |
| 53 | O | CH$_2$CH=CH$_2$ | CH$_3$ | SCH$_2$CH$_3$ | n.d. |
| 54 | O | CH$_2$C≡CH | CH$_3$ | SCH$_2$CH$_3$ | n.d. |
| 55 | O | cyclohexyl | CH$_3$ | SCH$_2$CH$_3$ | n.d. |
| 56 | O | CH$_2$C$_6$H$_5$ | CH$_3$ | SCH$_2$CH$_3$ | n.d. |
| 57 | O | OCH$_3$ | CH$_3$ | SCH$_2$CH$_3$ | n.d. |
| 58 | S | CH$_2$CH$_3$ | CH$_2$CH$_3$ | SCH$_2$CH$_3$ | n.d. |
| 59 | O | —CH$_2$CH$_2$CH$_2$CH$_2$— | | CF$_2$H | n.d. |
| 60 | O | —CH$_2$CH$_2$OCH$_2$CH$_2$— | | CF$_2$H | n.d. |
| 61 | O | CH$_3$ | CH$_3$ | CF$_2$H | n.d. |
| 62 | O | C$_6$H$_5$ | CH$_3$ | CF$_2$H | n.d. |
| 63 | O | CH$_2$CH$_2$CH$_3$ | CH$_2$CH$_3$ | CF$_2$H | 8.98(1H), 6.32(1H), 3.4–3.6(4H), 1.74(2H), 1.29(3H), 0.9–1.0(3H) |
| 64 | O | CH$_2$CH$_2$OCH$_3$ | CH$_3$ | CF$_2$H | n.d. |
| 65 | O | CH$_2$CH=CH$_2$ | CH$_3$ | CF$_2$H | n.d. |
| 66 | O | CH$_2$C≡CH | CH$_3$ | CF$_2$H | n.d. |
| 67 | O | cyclohexyl | CH$_3$ | CF$_2$H | n.d. |
| 68 | O | CH$_2$C$_6$H$_5$ | CH$_3$ | CF$_2$H | 9.03(1H), 7.34(5H), 6.32(1H), 4.71(2H), 3.22(3H) |
| 69 | O | OCH$_3$ | CH$_3$ | CF$_2$H | n.d. |
| 70 | S | CH$_2$CH$_3$ | CH$_2$CH$_3$ | CF$_2$H | n.d. |
| 71 | O | —CH$_2$CH$_2$CH$_2$CH$_2$— | | CF$_2$H | n.d. |
| 72 | O | —CH$_2$CH$_2$OCH$_2$CH$_2$— | | CF$_2$Br | n.d. |
| 73 | O | CH$_3$ | CH$_3$ | CF$_2$Br | n.d. |
| 74 | O | C$_6$H$_5$ | CH$_3$ | CF$_2$Br | n.d. |
| 75 | O | CH$_2$CH$_2$CH$_3$ | CH$_2$CH$_3$ | CF$_2$Br | n.d. |
| 76 | O | CH$_2$CH$_2$OCH$_3$ | CH$_3$ | CF$_2$Br | n.d. |
| 77 | O | CH$_2$CH=CH$_2$ | CH$_3$ | CF$_2$Br | n.d. |
| 78 | O | CH$_2$C≡CH | CH$_3$ | CF$_2$Br | n.d. |
| 79 | O | cyclohexyl | CH$_3$ | CF$_2$Br | n.d. |
| 80 | O | CH$_2$C$_6$H$_5$ | CH$_3$ | CF$_2$Br | n.d. |
| 81 | O | OCH$_3$ | CH$_3$ | CF$_2$Br | n.d. |
| 82 | S | CH$_2$CH$_3$ | CH$_2$CH$_3$ | CF$_2$Br | n.d. |
| 83 | O | —CH$_2$CH$_2$CH$_2$CH$_2$— | | Cl | n.d. |
| 84 | O | —CH$_2$CH$_2$OCH$_2$CH$_2$— | | Cl | n.d. |
| 85 | O | CH$_3$ | CH$_3$ | Cl | 9.0(1H), 3.4(3H), 3.3(3H) |
| 86 | O | C$_6$H$_5$ | CH$_3$ | Cl | 8.8(1H), 7.4(3H), 7.2(2H), 3.6(3H) |
| 87 | O | CH$_2$CH$_2$CH$_3$ | CH$_2$CH$_3$ | Cl | n.d. |
| 88 | O | CH$_2$CH$_2$OCH$_3$ | CH$_3$ | Cl | n.d. |
| 89 | O | CH$_2$CH=CH$_2$ | CH$_3$ | Cl | n.d. |
| 90 | O | CH$_2$C≡CH | CH$_3$ | Cl | n.d. |
| 91 | O | cyclohexyl | CH$_3$ | Cl | n.d. |
| 92 | O | CH$_2$C$_6$H$_5$ | CH$_3$ | Cl | n.d. |
| 93 | O | OCH$_3$ | CH$_3$ | Cl | 9.0(1H), 3.9(3H), 3.4(3H) |
| 94 | S | CH$_2$CH$_3$ | CH$_2$CH$_3$ | Cl | 9.08(1H), 4.01(2H), 3.54(2H), 1.45(3H), 1.39(3H) | n.d. = not determined

Pre-emergence Herbicidal Activity of Compounds of Formula (II)

As noted above, compounds of this invention have been found to be effective as herbicides, particularly as pre-emergence herbicides. Tables 5 to 8 summarize results of tests conducted as described below to determine the pre-emergence herbicidal activity, in the form of a GR$_{80}$ value, of illustrative compounds of this invention. The GR$_{80}$ value as used herein is not a true GR$_{80}$, instead being defined as the lowest tested rate (in g/ha) at which 80% or greater inhibition was observed in the test in question. Compounds of the invention were typically applied at rates of 300, 100, 30, and 10 g/ha. Where herbicidal activity was evident but 80% inhibition was not achieved at the highest rate tested, an asterisk (*) is shown in the following tables.

The pre-emergence tests were conducted by the following procedure. Topsoil was sieved to pass through a 1.27 cm screen. Fertilizer was added to the topsoil and the mixture was then sterilized by heating. The topsoil mixture was placed in a pot and compacted to a depth of 1.0 to 1.25 cm from the top of the pot. Seeds of each of several monocotyledonous and dicotyledonous annual plant species were placed on top of the soil. Additional soil was subsequently placed over the seeds to level-fill the pot. A known amount of each test compound dissolved or suspended in an appropriate organic solvent was diluted with a 50:50 mix of acetone and water and applied to the surface of the soil. After treatment the plants were placed in a greenhouse where they received 0.64 cm of overhead irrigation. All subsequent watering consisted of a light overhead mist and/or subirrigation as needed for germination and growth. Tables 5 and 6 below relate to warm season plant species which were placed after pre-emergence treatment in a greenhouse with a 30/21° C. day/night temperature regime. Tables 7 and 8 below relates to cool season plant species placed after pre-emergence treatment in a greenhouse or growth chamber with an 18/13° C. day/night temperature regime.

Approximately 14 days after planting and treating, the plants were observed and herbicidal efficacy recorded as percent inhibition by comparison with untreated plants.

The plant species usually regarded as weeds which were utilized in the tests are identified in the tables below according to the following legend, in which "d" indicates a dicotyledonous species and "m" a monocotyledonous species. All monocotyledonous species included in the tests herein are grasses.

| Warm Season Species | | | |
|---|---|---|---|
| ABUTH | velvetleaf | Abutilon theophrasti | d |
| AMARE | redroot pigweed | Amaranthus retroflexus | d |
| BRAPP | broadleaf signalgrass | Brachiaria platyphylla | m |
| CHEAL | common lambsquarters | Chenopodium album | d |
| CIRAR | canada thistle (seedling) | Cirsium arvense | d |
| CONAR | field bindweed | Convolvulus arvensis | d |
| DATST | jimsonweed | Datura stramonium | d |
| DIGSA | large crabgrass | Digitaria sanguinalis | m |
| ECHCG | barnyardgrass | Echinochloa crus-galli | m |
| IPOSS | annual morningglory | Ipomoea spp. | d |
| PANDI | fall panicum | Panicum dichotomiflorum | m |
| PANMI | wild proso millet | Panicum miliaceum | m |
| POROL | common purslane | Portulaca oleracea | d |
| SETFA | giant foxtail | Setaria faberi | m |
| SOLNI | black nightshade | Solanum nigrum | d |
| SORHA | johnsongrass (seedling) | Sorghum halepense | m |
| SORVU | shattercane | Sorghum vulgare | m |
| XANST | cocklebur | Xanthium strumarium | d |
| Cool season species | | | |
| AEGCY | jointed goatgrass | Aegilops cylindrica | m |
| AGRRE | quackgrass (seedling) | Elymus repens | m |
| AGSST | creeping bentgrass | Agrostis stolonifera | m |
| ALOMY | blackgrass | Alopecurus myosuroides | m |
| AVEFA | wild oat | Avena fatua | m |
| BROTE | downy brome | Bromus tectorum | m |
| GALAP | catchweed bedstraw | Galium aparine | d |
| KCHSC | kochia | Kochia scoparia | d |
| LAMPU | purple deadnettle | Lamium purpureum | d |
| LOLMG | annual ryegrass | Lolium multiflorum | m |
| POAAN | annual bluegrass | Poa annua | m |
| POLCO | wild buckwheat | Polygonum convolvulus | d |
| SASKR | russian thistle | Salsola kali | d |
| SETVI | green foxtail | Setaria viridis | m |
| SINAR | wild mustard | Sinapis arvensis | d |
| STEME | common chickweed | Stellaria media | d |
| VERPE | creeping speedwell | Veronica persicaria | d |

TABLE 5

Pre-emergence activity (GR$_{80}$, g/ha) on warm season dicotyledonous species

| Example no. | ABUTH | SOLNI | AMARE | DATST | CHEAL | CONAR | POROL | CIRAR |
|---|---|---|---|---|---|---|---|---|
| 1 | 300 | 100 | 30 | 300 | 300 | 300 | 100 | 100 |
| 2 |  | 300 | 30 | 300 | 100 | 300 | 100 | 300 |
| 3 |  | 100 | 100 | 100 | 100 | 300 | 100 | 30 |
| 4 |  | 300 | 100 | 300 | 30 |  | 100 | 30 |
| 5 |  | 300 | 100 |  | 300 |  |  | 100 |
| 6 |  |  |  |  | 300 |  |  | 300 |
| 7 |  |  | 300 | 300 | 300 |  |  |  |
| 8 | 300 | 100 | 100 | 300 | 100 | 100 | 300 | 300 |
| 9 |  | 100 | 300 | 300 | 300 | 300 | 300 | 100 |
| 10 |  | 300 | 100 |  | 300 |  |  | 300 |
| 11 |  | 300 | 100 |  | 300 |  |  | 300 |
| 12 |  |  |  |  |  |  |  |  |
| 13 | 300 | 300 |  |  | 300 |  |  |  |
| 14 |  | 300 | 300 |  | 300 | * | 300 | 300 |
| 15 | 300 | 100 | 30 | 300 |  |  | 100 | 30 |
| 16 | 300 | 100 | 300 | 300 | 300 | 300 | 100 |  |
| 17 | 300 | 100 | 300 |  | 100 |  | 300 |  |
| 18 | * | 100 | 300 | 300 | 300 |  | 100 | 300 |
| 19 |  | 300 | * | * | 100 | * | 300 | 300 |
| 20 | 300 | 100 |  |  | 300 | * | 300 | 100 |
| 21 |  |  |  |  |  |  |  |  |
| 22 |  |  |  |  | 300 |  |  |  |
| 23 |  |  | 300 |  | 300 | 300 | 300 | 300 |
| 24 |  |  |  |  | 300 | 300 | 100 |  |
| 25 |  |  |  |  |  |  |  |  |

TABLE 5-continued

Pre-emergence activity (GR$_{80}$, g/ha) on warm season dicotyledonous species

| Example no. | ABUTH | SOLNI | AMARE | DATST | CHEAL | CONAR | POROL | CIRAR |
|---|---|---|---|---|---|---|---|---|
| 26 | | | | | | | | |
| 27 | | | | | 300 | | | |
| 28 | | | 300 | | | | | |
| 29 | | | | | | | | |
| 30 | | | | | | | 300 | 300 |
| 31 | | | | | | | | |
| 32 | | 300 | 300 | | 300 | | 100 | 300 |
| 33 | | | | 300 | | | | |
| 34 | | | | | | | | |
| 35 | | | | | | | | |
| 36 | | | | | 300 | | | |
| 37 | | | | | | | 300 | |
| 38 | | | | | | | | |
| 39 | | | 300 | | 300 | | 10o | |
| 40 | | | | | | | | |
| 41 | | | | | | | | |
| 42 | | | | | | | | |
| 43 | | | | | | | 300 | 300 |
| 44 | 300 | 30 | | | | | | |
| 45 | | | | | 300 | | | |
| 46 | | | | | | | | |
| 47 | | 300 | | | 300 | 300 | 300 | |
| 48 | | | | 300 | | | | |
| 49 | | | | | 300 | 300 | 300 | |
| 50 | | | | | | | | |
| 51 | | 300 | | | 10 | | 300 | |
| 52 | | 300 | | | | | | |
| 53 | | | | | | | | |
| 54 | | | | | | | | |
| 55 | 300 | 300 | | | 300 | | 300 | |
| 56 | | | | 300 | | | | |
| 57 | | | | | | | | |
| 58 | | | | 300 | 300 | | | |
| 59 | | 300 | 100 | | 100 | | | 300 |
| 60 | | | | | | | | |
| 61 | | | | | 300 | | 300 | 300 |
| 62 | | | | | | | | |
| 63 | 300 | 300 | 100 | | 100 | | 300 | 300 |
| 64 | | | | | | | 300 | |
| 65 | | | | | 300 | | | |
| 66 | 300 | | | | | | | |
| 67 | | | 300 | | 100 | | 300 | |
| 68 | | 300 | | | | | | |
| 69 | | | | | | | | |
| 70 | | 300 | | | 300 | | 300 | 300 |
| 71 | | 300 | 300 | | 30 | | 300 | 300 |
| 72 | | | | | | | | |
| 73 | | | | | | | | |
| 74 | | | | | | | | |
| 75 | | | | | 300 | | 300 | |
| 76 | | 300 | | | | | 300 | |
| 77 | | | | | | | | |
| 78 | | 300 | | | | | | |
| 79 | | | | | | | | |
| 80 | | | | | | | | |
| 81 | | | | | | | | |
| 82 | | | | | 300 | | 30 | |
| 83 | | 300 | 300 | | 100 | 300 | 100 | 100 |
| 84 | | | | 300 | | | | |
| 85 | | | | | | | | |
| 86 | | | | | | | | |
| 87 | | 100 | 300 | | 300 | | 100 | 300 |
| 88 | | | 100 | | | | | |
| 89 | | | | | | | 100 | |
| 90 | | | | | | | | |
| 91 | 300 | | | | | | | |
| 92 | | | | | 300 | 300 | | |
| 93 | 100 | | | | | | | |
| 94 | 100 | 100 | 10 | 300 | 30 | 100 | 30 | 30 |

Blank = no activity at any rate tested
* = activity observed, at least at highest rate, but <80% inhibition

TABLE 6

Pre-emergence activity (GR$_{80}$, g/ha) on warm season monocotyledonous species

| Example no. | ECHCG | PANMI | SORHA | SETFA | PANDI | SORVU | BRAPP | DIGSA |
|---|---|---|---|---|---|---|---|---|
| 1 | 30 | 100 | 30 | 100 | 30 | * | * | 30 |
| 2 | 30 | 30 | 100 | 100 | 30 | 300 | 300 | 300 |
| 3 | 30 | 30 | 100 | 100 | 100 | 100 | 100 | 100 |
| 4 | 100 | 100 | 30 | 30 | 30 | * | 300 | 100 |
| 5 | 300 | 100 | 100 | 100 | no data | | 300 | 100 |
| 6 | * | 300 | 100 | * | 300 | * | * | 300 |
| 7 | 300 | 300 | 300 | 300 | 300 | | 300 | 300 |
| 8 | 100 | 100 | 100 | 100 | no data | 100 | 100 | 100 |
| 9 | 300 | 100 | 100 | 100 | no data | 300 | 300 | 100 |
| 10 | 300 | 300 | 100 | 100 | 300 | | 300 | 100 |
| 11 | * | 300 | 300 | | 300 | * | | |
| 12 | * | * | | | | * | * | |
| 13 | 300 | 300 | | * | 300 | * | 300 | |
| 14 | 300 | 100 | 300 | 100 | 100 | * | 300 | 100 |
| 15 | 100 | 30 | 100 | 100 | 100 | * | 300 | 30 |
| 16 | 100 | 30 | 100 | 30 | 100 | 100 | 300 | 30 |
| 17 | 100 | 100 | 100 | 100 | 100 | 100 | 300 | 100 |
| 18 | 100 | 30 | 100 | 100 | no data | * | 300 | 100 |
| 19 | 300 | 100 | 100 | 300 | no data | 300 | 300 | 100 |
| 20 | 300 | 100 | 300 | 100 | 300 | 300 | 300 | 100 |
| 21 | | * | | | | * | | |
| 22 | | | | | 300 | * | | |
| 23 | | 100 | 300 | 100 | no data | | | 300 |
| 24 | | | | | no data | | 100 | |
| 25 | | | | | no data | | | |
| 26 | | | | | no data | | | |
| 27 | | 100 | | | no data | | | |
| 28 | | 300 | | | no data | | 300 | 300 |
| 29 | | | | | no data | | | |
| 30 | | 100 | | 300 | no data | | 300 | 300 |
| 31 | | | | | no data | | | 300 |
| 32 | 300 | 300 | 30 | 300 | no data | 300 | | 300 |
| 33 | | 300 | | | no data | | | |
| 34 | | | | | no data | | | |
| 35 | | | | | no data | | | |
| 36 | | | | | no data | | | |
| 37 | 300 | 300 | 300 | | no data | | | 300 |
| 38 | | | | | no data | | | |
| 39 | 300 | 300 | 100 | 100 | no data | | | |
| 40 | 300 | 300 | 300 | 300 | 300 | | | |
| 41 | | 300 | | | no data | | | |
| 42 | | 300 | | | no data | | | |
| 43 | | 100 | | 100 | 100 | | 300 | |
| 44 | | 300 | | | | | | |
| 45 | | | | | | | | |
| 46 | | 300 | 300 | 300 | 300 | | | |
| 47 | 300 | 100 | 300 | 300 | 300 | | 300 | |
| 48 | | | | | no data | | | |
| 49 | 300 | 300 | 300 | 300 | 300 | 300 | 300 | |
| 50 | | 300 | | | no data | | | |
| 51 | 100 | 100 | 100 | 100 | 100 | 30 | 100 | 100 |
| 52 | 300 | 100 | | 300 | 30 | | | |
| 53 | | 300 | | | no data | | | |
| 54 | | 300 | | | no data | | | |
| 55 | 300 | 100 | 300 | 300 | no data | 300 | 300 | 300 |
| 56 | | | | | no data | | | |
| 57 | | | | | no data | | | 300 |
| 58 | | | | | no data | | | |
| 59 | 300 | 100 | 100 | 300 | no data | | 100 | 30 |
| 60 | | | | | no data | | | |
| 61 | 300 | 300 | | | no data | | | |
| 62 | | | | | no data | | | |
| 63 | 100 | 100 | 100 | 100 | no data | | 300 | 300 |
| 64 | | 100 | | 300 | no data | | 300 | 300 |
| 65 | | 300 | | | no data | | | |
| 66 | | | | | no data | | | |
| 67 | 300 | 100 | 300 | 300 | no data | | | |
| 68 | | 300 | | 300 | no data | | | |
| 69 | | | | | no data | | | |
| 70 | | 300 | | 300 | no data | | | 300 |
| 71 | | 300 | 300 | 300 | no data | | | |
| 72 | | | | | no data | | | |
| 73 | 300 | 100 | 300 | | no data | | | |
| 74 | | 300 | | | no data | | | |

TABLE 6-continued

Pre-emergence activity (GR$_{80}$, g/ha) on warm season monocotyledonous species

| Example no. | ECHCG | PANMI | SORHA | SETFA | PANDI | SORVU | BRAPP | DIGSA |
|---|---|---|---|---|---|---|---|---|
| 75 | 100 | 100 | 300 | 300 | no data | 300 | 300 | 300 |
| 76 | | 100 | | 300 | no data | | | 300 |
| 77 | | | | | no data | | | |
| 78 | | | | | no data | | | |
| 79 | 300 | 300 | | | no data | | | |
| 80 | | 300 | | | no data | | | |
| 81 | | | | | no data | | | |
| 82 | | 300 | 300 | 300 | no data | | 300 | |
| 83 | | 100 | 300 | 300 | no data | 300 | 100 | 100 |
| 84 | | | | | no data | | | |
| 85 | | | | | no data | | | |
| 86 | | | | | no data | | | |
| 87 | 100 | 30 | 100 | 300 | no data | 300 | 300 | 300 |
| 88 | | 300 | | | no data | | | 300 |
| 89 | | 300 | | | no data | | | 100 |
| 90 | | | | | no data | | | |
| 91 | | 100 | | | no data | 300 | | |
| 92 | | | | | no data | | | |
| 93 | | | | | no data | | | |
| 94 | | 100 | 300 | 100 | no data | 100 | 10 | 300 |

Blank = no activity at any rate tested
* = activity observed, at least at highest rate, but <80% inhibition

TABLE 7

Pre-emergence activity (GR$_{80}$, g/ha) on cool season dicotyledonous species

| Example no. | GALAP | POLCO | SINAR | KCHSC | VERPE | SASKR | STEME | LAMPU |
|---|---|---|---|---|---|---|---|---|
| 1 | 100 | | 100 | 300 | 100 | 300 | 100 | 30 |
| 2 | 100 | | 30 | 300 | 10 | 100 | 10 | 10 |
| 3 | 100 | | 300 | 300 | 100 | | 30 | 100 |
| 4 | 100 | 300 | 30 | 100 | 10 | 30 | 10 | 30 |
| 5 | | | 100 | | 100 | 300 | | |
| 6 | 100 | 300 | 300 | 300 | 300 | | 300 | 100 |
| 7 | | | * | | | | | 30 |
| 8 | | | | | 30 | 300 | | |
| 9 | | | 300 | 300 | 100 | 300 | 300 | 300 |
| 10 | | | 100 | no data | 100 | 100 | 300 | 100 |
| 11 | | | 100 | no data | 100 | 300 | | 100 |
| 12 | | | | no data | | | 300 | 300 |
| 13 | 100 | | | no data | 300 | | 100 | 100 |
| 14 | 30 | 300 | | no data | 300 | | 300 | 300 |
| 15 | no data | no data | no data | no data | no data | no data | no data | no data |
| 16 | 100 | | 100 | no data | 100 | 100 | 300 | 100 |
| 17 | 100 | 100 | 100 | no data | 100 | 100 | 100 | 100 |
| 18 | 300 | 300 | 300 | no data | 300 | 300 | 30 | 300 |
| 19 | 300 | | 30 | no data | 300 | 100 | 10 | 30 |
| 20 | | * | | | | | | 100 |
| 21 | 300 | | | no data | 300 | | | 300 |
| 22 | | | | no data | 300 | | | |
| 23 | 300 | 30 | 300 | no data | | | 100 | 100 |
| 24 | | | | no data | | | | |
| 25 | 300 | | | no data | | | | 300 |
| 26 | 300 | 300 | | no data | 300 | 300 | | 300 |
| 27 | 300 | 30 | | no data | 300 | 300 | | 300 |
| 28 | 30 | | 10 | no data | 10 | 30 | 10 | 30 |
| 29 | | | 300 | no data | 100 | 300 | 300 | 300 |
| 30 | 100 | 100 | 100 | no data | 10 | 10 | 10 | 10 |
| 31 | | | | no data | | | | |
| 32 | 100 | | 100 | no data | 300 | | 300 | |
| 33 | | | | no data | 300 | 300 | 100 | 30 |
| 34 | | 300 | 300 | no data | 300 | 300 | | 300 |
| 35 | 100 | 100 | 100 | no data | 100 | | | 300 |
| 36 | 300 | | | no data | | | | 300 |
| 37 | | | | no data | | | 300 | 300 |
| 38 | | | | no data | | | | |
| 39 | 100 | 100 | 30 | no data | 10 | 100 | 30 | 30 |
| 40 | | | 100 | no data | 100 | 300 | 300 | |
| 41 | | | | no data | 100 | | | |

TABLE 7-continued

Pre-emergence activity (GR$_{80}$, g/ha) on cool season dicotyledonous species

| Example no. | GALAP | POLCO | SINAR | KCHSC | VERPE | SASKR | STEME | LAMPU |
|---|---|---|---|---|---|---|---|---|
| 42 | 300 | | | no data | | | 300 | 300 |
| 43 | 300 | | | no data | 300 | | 300 | 300 |
| 44 | | | | no data | 100 | | | |
| 45 | | 100 | 300 | no data | | | 300 | |
| 46 | 300 | 300 | | no data | 100 | 300 | 300 | 100 |
| 47 | 300 | | 300 | no data | 10 | 100 | 30 | 30 |
| 48 | 300 | 300 | | no data | | | 300 | |
| 49 | 300 | | 300 | no data | 300 | | 300 | 300 |
| 50 | 100 | | | no data | | | 300 | |
| 51 | 100 | 100 | | no data | 10 | 100 | 10 | 10 |
| 52 | | | 300 | no data | 30 | 100 | | |
| 53 | 300 | | | no data | | | | |
| 54 | | 100 | | no data | 300 | | | |
| 55 | | 300 | | no data | | | | |
| 56 | | | | no data | | | | |
| 57 | 300 | 100 | 30 | no data | 10 | 30 | 30 | |
| 58 | 300 | 300 | | no data | 300 | 300 | 300 | 300 |
| 59 | 100 | 300 | | no data | | | 300 | 100 |
| 60 | | | | no data | | | | |
| 61 | 100 | | 300 | no data | 100 | 100 | 300 | 300 |
| 62 | | | | no data | | | | 300 |
| 63 | 30 | 300 | 30 | no data | 30 | 30 | 30 | 30 |
| 64 | 300 | 100 | 100 | no data | 30 | 10 | 100 | 300 |
| 65 | 30 | 100 | 300 | no data | 100 | | 300 | 100 |
| 66 | | 300 | | no data | 100 | 300 | | |
| 67 | 300 | 300 | | no data | 100 | | | |
| 68 | 300 | 300 | 300 | no data | | | | |
| 69 | 100 | 100 | 30 | no data | 100 | | 300 | |
| 70 | | 300 | 300 | no data | | 300 | | |
| 71 | 100 | 300 | | no data | | | 300 | 300 |
| 72 | | 300 | | no data | | | | |
| 73 | 100 | | 100 | no data | 100 | 100 | 300 | 300 |
| 74 | | | 300 | no data | 300 | 300 | | 300 |
| 75 | 300 | | 30 | no data | 10 | 10 | 30 | 30 |
| 76 | 100 | 300 | 10 | no data | 30 | 30 | 300 | 100 |
| 77 | | | | no data | | | | |
| 78 | | | 30 | no data | 30 | 100 | | 100 |
| 79 | 300 | 300 | 300 | no data | 30 | | 100 | 100 |
| 80 | | | | no data | | | | |
| 81 | | | 30 | no data | 100 | 100 | 30 | 100 |
| 82 | | 300 | 300 | no data | 300 | | 300 | 300 |
| 83 | 100 | 300 | | no data | | 300 | 300 | 100 |
| 84 | | 300 | | no data | | | | 300 |
| 85 | | | 30 | no data | 100 | 100 | 30 | 100 |
| 86 | 300 | | 300 | no data | 100 | 300 | | 100 |
| 87 | 300 | | | no data | 100 | | | 100 |
| 88 | 100 | 300 | 30 | no data | 30 | 30 | 10 | 10 |
| 89 | 300 | 100 | 300 | no data | | 300 | 100 | 100 |
| 90 | | | 300 | no data | 10 | 30 | | |
| 91 | 100 | 100 | 10 | no data | 10 | 30 | 30 | 30 |
| 92 | | | | no data | | | | |
| 93 | | | | no data | 300 | | | |
| 94 | | 10 | | no data | | | 300 | 300 |

Blank = no activity at any rate tested
* = activity observed, at least at highest rate, but <80% inhibition

TABLE 8

Pre-emergence activity (GR$_{80}$, g/ha) on cool season monocotyledonous species

| Example no. | ALOMY | SETVI | LOLMG | BROTE | AVEFA | AEGCY | AGSST | AGRRE |
|---|---|---|---|---|---|---|---|---|
| 1 | 300 | 30 | 100 | 300 | 100 | | 30 | 300 |
| 2 | 100 | 30 | 300 | 300 | | | 30 | 100 |
| 3 | 100 | 100 | | * | | | 30 | |
| 4 | 300 | 30 | 300 | 300 | 30 | * | 10 | 30 |
| 5 | * | 100 | | | | | 30 | * |
| 6 | 100 | 300 | 300 | | 300 | | 100 | 300 |
| 7 | * | | | | | | 300 | 300 |
| 8 | 100 | 100 | | * | 300 | | 30 | |

TABLE 8-continued

Pre-emergence activity (GR$_{80}$, g/ha) on cool season monocotyledonous species

| Example no. | ALOMY | SETVI | LOLMG | BROTE | AVEFA | AEGCY | AGSST | AGRRE |
|---|---|---|---|---|---|---|---|---|
| 9 | 300 | 100 | * | 100 | 300 | | 30 | |
| 10 | 300 | 300 | | | | | 100 | |
| 11 | 300 | 300 | | | | | | |
| 12 | | | | | | | 300 | |
| 13 | 300 | 100 | | 300 | 300 | | 100 | |
| 14 | 100 | 30 | | | 300 | | 30 | * |
| 15 | no data | no data | no data | no data | no data | no data | no data | no data |
| 16 | 100 | 300 | 300 | | 300 | | 30 | * |
| 17 | 100 | 100 | 100 | 100 | 100 | | 100 | |
| 18 | 300 | 30 | 300 | 300 | * | | 30 | 300 |
| 19 | 100 | 100 | 300 | * | * | | 30 | * |
| 20 | 100 | 100 | | | | | 300 | |
| 21 | | | | | | | | |
| 22 | | | | | | | 300 | |
| 23 | 300 | 100 | 300 | | | 300 | 100 | |
| 24 | | | | | | | | |
| 25 | | | | | | | | |
| 26 | | 300 | | | 300 | | 30 | |
| 27 | 300 | | | | | | | |
| 28 | 30 | 30 | 300 | | | | 30 | |
| 29 | | | | | | | 300 | |
| 30 | 300 | 300 | | | 100 | 100 | 30 | |
| 31 | | | | | | | | |
| 32 | 300 | 100 | 300 | | | | 300 | |
| 33 | | | | | | | 300 | |
| 34 | | 300 | | 300 | | | | |
| 35 | | | | | | | | |
| 36 | | | | | | | | |
| 37 | | | | | | | 100 | |
| 38 | | | | | | | | |
| 39 | 300 | 100 | 300 | | | | 30 | |
| 40 | | | | 100 | | | 30 | |
| 41 | 300 | | | | | | 30 | |
| 42 | | | | | | | 100 | |
| 43 | 300 | 300 | | | | | 100 | |
| 44 | | | | | | | | |
| 45 | | 300 | | | | | | |
| 46 | | 300 | | | | | 300 | |
| 47 | 300 | 300 | 300 | | | | 30 | |
| 48 | | | | | | | | |
| 49 | | 300 | | | 300 | | 100 | |
| 50 | | | | | | | 30 | |
| 51 | 300 | 100 | 100 | | 300 | 300 | 10 | 300 |
| 52 | 300 | 300 | 300 | 300 | | | 300 | 100 |
| 53 | | 300 | | | | | 300 | |
| 54 | | | | | | | | |
| 55 | | 300 | | | | | 300 | |
| 56 | | 100 | | | | | 100 | |
| 57 | 300 | 300 | 30 | | | | | |
| 58 | | 300 | | | | | | |
| 59 | 300 | 300 | | | | | 300 | |
| 60 | | | | | | | | |
| 61 | 100 | 300 | | | | | 100 | |
| 62 | | | | | | | | |
| 63 | 300 | 100 | 100 | | 300 | | 10 | |
| 64 | 300 | 100 | | | | | 100 | |
| 65 | 100 | 100 | | | | | 300 | |
| 66 | | | | | | | | |
| 67 | | 300 | | | | | 100 | |
| 68 | | 300 | | | | | | |
| 69 | 300 | 100 | 300 | 300 | | | | |
| 70 | | 300 | | | | | 300 | |
| 71 | 300 | 100 | | | | | 100 | |
| 72 | | | | | | | | |
| 73 | | 300 | | | | | 100 | |
| 74 | | | | | | | | |
| 75 | | 30 | 300 | 300 | | | 30 | |
| 76 | 300 | 100 | | | 300 | 300 | 100 | 100 |
| 77 | | | | | | | 300 | |
| 78 | | | | | | | | |
| 79 | | 300 | | | | | 100 | |
| 80 | | 300 | | | | | | |
| 81 | | | | 30 | | | 100 | |
| 82 | | 100 | | | | | 300 | |

TABLE 8-continued

Pre-emergence activity (GR$_{80}$, g/ha) on cool season monocotyledonous species

| Example no. | ALOMY | SETVI | LOLMG | BROTE | AVEFA | AEGCY | AGSST | AGRRE |
|---|---|---|---|---|---|---|---|---|
| 83 | 300 | 300 | | | | | 100 | |
| 84 | | | | | | | | |
| 85 | | 300 | 100 | 100 | | | 100 | |
| 86 | | | | | | | | |
| 87 | 100 | 100 | | | | | 100 | |
| 88 | 300 | 100 | 300 | 300 | | | 100 | |
| 89 | | 100 | | | | | 100 | |
| 90 | | | | | | | | |
| 91 | 300 | 300 | 300 | 300 | | | 100 | |
| 92 | | | | | | | | |
| 93 | | | | | | | | |
| 94 | 10 | | | | | | 300 | |

Blank = no activity at any rate tested
* = activity observed, at least at highest rate, but <80% inhibition Pre-plant Incorporated Herbicidal Activity of Compounds of Formula (II)

In another set of tests, the pre-plant incorporated (PPI) activity of compounds of this invention was evaluated on the same species as for the pre-emergence tests described above. In the PPI tests the following procedure, designed to simulate PPI application, was used.

A pre-prepared topsoil mixture (described above) was placed in a pot and compacted to a depth of 1.0 to 1.25 cm from the top of the pot. Seeds of each of several monocotyledonous and dicotyledonous annual plant species were placed on top of the soil. A sufficient quantity of soil to cover the seeds and level fill the pot was weighed into an open container. A known amount of the test compound was dissolved or suspended in an organic solvent and applied by spraying to this cover soil. The cover soil was thoroughly mixed to distribute the test compound throughout the cover soil, and was then applied as a cover layer over the seeds. Untreated soil was used as a cover layer for control pots.

After treatment the plants were placed in a greenhouse where they received 0.64 cm of overhead irrigation. All subsequent watering consisted of a light overhead mist and/or subirrigation as needed for germination and growth. Tables 9 and 10 below relate to warm season plant species which were placed after pre-emergence treatment in a greenhouse with a 30/21° C. day/night temperature regime. Tables 11 and 12 below relates to cool season plant species placed after pre-emergence treatment in a greenhouse or growth chamber with an 18/13° C. day/night temperature regime. Only the compounds of Examples 1, 6, 8, 11, 13 and 15–20 were included in PPI tests.

Approximately 14 days after planting and treating, the plants were observed and herbicidal efficacy recorded as percent inhibition by comparison with untreated plants.

TABLE 9

PPI activity (GR$_{80}$, g/ha) on warm season dicotyledonous species

| Example no. | ABUTH | SOLNI | AMARE | DATST | CHEAL | CONAR | POROL | CIRAR |
|---|---|---|---|---|---|---|---|---|
| 1 | 100 | 30 | 30 | 30 | 300 | 100 | 30 | 100 |
| 6 | | 100 | 100 | 300 | 100 | * | 300 | 100 |
| 8 | 300 | 100 | 100 | 100 | 30 | 300 | 100 | 100 |
| 11 | 300 | 300 | 100 | 100 | 100 | 100 | 300 | 100 |
| 13 | 100 | 100 | 100 | 300 | 30 | * | 100 | 100 |
| 15 | 100 | 100 | 100 | 300 | 100 | * | 100 | 100 |
| 16 | 100 | 30 | 10 | 100 | 30 | 100 | 10 | 30 |
| 17 | 100 | 30 | 10 | 300 | 300 | * | 30 | 300 |
| 18 | 100 | 300 | 300 | 300 | 30 | 100 | 100 | 30 |
| 19 | 30 | 100 | 100 | 300 | 100 | 300 | 100 | 300 |
| 20 | 300 | 100 | 300 | 300 | 30 | * | 100 | 100 |

Blank = no activity at any rate tested
* = activity observed, at least at highest rate, but <80% inhibition

TABLE 10

PPI activity (GR$_{80}$, g/ha) on warm season monocotyledonous species

| Example no. | ECHCG | PANMI | SORHA | SETFA | PANDI | SORVU | BRAPP | DIGSA |
|---|---|---|---|---|---|---|---|---|
| 1 | 30 | 30 | 30 | 30 | 100 | 100 | 100 | 100 |
| 6 | 100 | 100 | 100 | 100 | 100 | 300 | 300 | 100 |

TABLE 10-continued

PPI activity (GR$_{80}$, g/ha) on warm season monocotyledonous species

| Example no. | ECHCG | PANMI | SORHA | SETFA | PANDI | SORVU | BRAPP | DIGSA |
|---|---|---|---|---|---|---|---|---|
| 8 | 30 | 10 | 30 | 30 | 30 | 300 | 30 | 30 |
| 11 | * | * | 300 | 300 | no data | 300 | 300 | 300 |
| 13 | 100 | 100 | 100 | 30 | 30 | 300 | 100 | 30 |
| 15 | 100 | 30 | 30 | 30 | 100 | 300 | 100 | 100 |
| 16 | 30 | 30 | 10 | 10 | 10 | 30 | 10 | 10 |
| 17 | 30 | 10 | 10 | 10 | 300 | * | 100 | 30 |
| 18 | 30 | 100 | 300 | 100 | no data | 100 | 100 | 30 |
| 19 | 30 | 100 | 100 | 30 | no data | 300 | 300 | 30 |
| 20 | 300 | 100 | 100 | 100 | 100 | * | 100 | 100 |

Blank = no activity at any rate tested
* = activity observed, at least at highest rate, but <80% inhibition

TABLE 11

PPI activity (GR$_{80}$, g/ha) on cool season dicotyledonous species

| Example no. | GALAP | POLCO | SINAR | KCHSC | VERPE | SASKR | STEME | LAMPU |
|---|---|---|---|---|---|---|---|---|
| 1 | 100 | * | 100 | 100 | 30 | 100 | 100 | 100 |
| 6 | 100 | 300 | 300 | 300 | 100 | 300 | 100 | 300 |
| 8 | 100 | 300 | 100 | 100 | 100 | 100 | 30 | 100 |
| 11 | 300 | * | 100 | no data | | 100 | 300 | 300 |
| 13 | 300 | * | | * | 100 | 300 | * | 30 |
| 15 | 30 | 300 | 100 | 100 | 300 | 100 | 300 | 300 |
| 16 | 100 | 100 | 10 | 30 | 100 | 30 | 300 | 10 |
| 17 | 100 | 100 | 30 | 30 | 10 | 30 | 10 | 30 |
| 18 | 100 | 100 | 10 | no data | | 30 | 100 | 10 |
| 19 | 100 | * | 300 | no data | | 30 | 100 | 100 |
| 20 | | * | * | | 30 | 300 | * | 100 |

Blank = no activity at any rate tested
* = activity observed, at least at highest rate, but <80% inhibition

TABLE 12

PPI activity (GR$_{80}$, g/ha) on cool season monocotyledonous species

| Example no. | ALOMY | SETVI | LOLMG | BROTE | AVEFA | AEGCY | AGSST | AGRRE |
|---|---|---|---|---|---|---|---|---|
| 1 | 100 | 100 | 300 | 300 | 300 | | 30 | * |
| 6 | 300 | 300 | 300 | * | 300 | | 100 | 300 |
| 8 | 100 | 30 | 100 | 300 | 100 | | 30 | 300 |
| 11 | 300 | 300 | | | | | 300 | * |
| 13 | 100 | 100 | * | * | | | 30 | * |
| 15 | 100 | 100 | 100 | * | 300 | | 100 | 300 |
| 16 | 30 | 10 | 300 | 300 | 300 | 300 | 10 | 300 |
| 17 | 30 | 30 | 100 | 100 | 100 | 100 | 10 | 100 |
| 18 | 100 | 30 | 100 | 300 | 300 | * | 10 | 100 |
| 19 | 30 | 30 | 300 | 300 | 300 | 300 | 10 | 100 |
| 20 | 100 | 30 | * | 300 | 300 | * | 30 | 300 |

Blank = no activity at any rate tested
* = activity observed, at least at highest rate, but <80% inhibition Post-emergence Herbicidal Activity of Compounds of Formula (II)

In another set of tests, the post-emergence activity of compounds of this invention was evaluated on the cool season species listed above. The following procedure was used.

A pre-prepared topsoil mixture (described above) was placed in a pot and compacted to a depth of 1.0 to 1.25 cm from the top of the pot. Seeds of each of several monocotyledonous and dicotyledonous annual plant species were placed on top of the soil. The seeds were covered with a mixture of 50% topsoil and 50% Rediearth™ in sufficient quantity to level-fill the pots. The pots were then placed on a greenhouse bench and subirrigated as needed.

When plants growing from the seeds had emerged and reached a suitable growth stage for post-emergence treatment, typically 9 to 14 days after planting, aboveground parts of the plants were subjected to a pre-treatment involving abrasion to create greater opportunity for foliar uptake of subsequently applied compounds. Abrasion was performed using garnet 200w particles applied with a Sears Craftsman hand-held sandblaster operated at approximately 850 kPa (50 psig) pressure.

A known amount of each test compound dissolved or suspended in an appropriate organic solvent was diluted with a 50:50 mix of acetone and water and applied to the plants by spraying with a standard spray nozzle in a spray volume of 3,100 l/ha at a spray pressure of 511 kPa (30 psig). Only the compounds of Examples 1, 8–15 and 17–22 were included in post-emergence tests. Application rates for these compounds were 300, 100, 30 and 10 g/ha. Control plants were abraded but not sprayed.

After treatment the plants were placed in a greenhouse with an 18/13° C. day/night temperature regime and were subsequently watered as needed for growth. Approximately 14 days after treatment, the plants were observed and herbicidal efficacy recorded as percent inhibition by comparison with control plants. $GR_{80}$ values were assigned for each compound as described above for the pre-emergence tests. Data are presented in Tables 13 and 14 below.

Selectivity of Compounds of Formula (II)

Additional pre-emergence and PPI tests were conducted by the procedures described above, on warm and cool season weed species in the presence of crop species, to assess herbicidal selectivity. Crop species included in warm season tests were corn (*Zea mays*, ZEAMX), rice (*Oryza sativa*, ORYSA) and soybean (*Glycine max*, GLYMX). Crop species included in cool season tests were wheat (*Triticum aestivum*, TRZAW), barley (*Hordeunm vulgare*, HORVX) and oilseed rape (*Brassica napus*, BRSNS).

Tables 5–17 present data as percent inhibition for each application rate tested. Tables 15 and 16 relate to pre-emergence and PPI tests respectively on warm season species. Table 17 relates to pre-emergence tests on cool season species.

TABLE 13

Post-emergence activity ($GR_{80}$, g/ha) on cool season dicotyledonous species

| Example no. | GALAP | POLCO | SINAR | KCHSC | VERPE | SASKR | STEME | LAMPU |
|---|---|---|---|---|---|---|---|---|
| 1 | | | | 100 | 300 | | | |
| 8 | | | | no data | | | | |
| 9 | | | | no data | | | | |
| 10 | | | | no data | | | | |
| 11 | | | | no data | | | | |
| 12 | 300 | | | no data | | | | |
| 13 | | | | no data | | | | |
| 14 | | | | no data | | | | |
| 15 | | | | 100 | | 100 | | |
| 17 | | | | no data | | | | |
| 18 | | | | no data | | | | |
| 19 | | | | no data | | | | |
| 20 | | | | no data | | | | |
| 21 | | | | no data | | | | |
| 22 | | | | no data | | | | |

Blank = no activity at any rate tested
* = activity observed, at least at highest rate, but <80% inhibition

TABLE 14

Post-emergence activity ($GR_{80}$, g/ha) on warm season monocotyledonous species

| Example no. | ALOMY | SETVI | LOLMG | BROTE | AVEFA | AEGCY | AGSST | AGRRE |
|---|---|---|---|---|---|---|---|---|
| 1 | | | | | | | | |
| 8 | | | | | | | | |
| 9 | | | | | | | | |
| 10 | | | | | | | | |
| 11 | | | | | | | | |
| 12 | | | | | | | | |
| 13 | | | | | | | | |
| 14 | | | | | | | | 300 |
| 15 | | | | | | | | |
| 17 | | | | | | | | 300 |
| 18 | | | | | | | | |
| 19 | | | | | | | | |
| 20 | | | | | | | | |
| 21 | | | | | | | | |
| 22 | | | | | | | | |

Blank = no activity at any rate tested
* = activity observed, at least at highest rate, but <80% inhibition

TABLE 15

Percent inhibition of warm season crops and weeds (pre-emergence application)

| Example no. | Rate g/ha | Crops | | | Weeds | | | | | |
|---|---|---|---|---|---|---|---|---|---|---|
| | | ZEAMX | GLYMX | ORYSA | ECHCG | ABUTH | PANMI | SOLNI | SORHA | AMARE |
| 1 | 900 | 10 | 0 | 10 | 95 | 0 | 90 | 20 | 99 | 90 |
| | 300 | 0 | nd | nd | 80 | 0 | 100 | 0 | 70 | 50 |
| | 100 | 0 | 0 | 0 | 45 | nd | 30 | 0 | 50 | 60 |
| | 30 | 0 | 0 | 0 | 10 | 0 | 0 | 0 | 0 | 0 |
| | 10 | 0 | 0 | 0 | 0 | 0 | 0 | 0 | 0 | 0 |
| 15 | 900 | 0 | 10 | 0 | 70 | 0 | 99 | 0 | 100 | 95 |
| | 300 | 0 | 0 | 0 | 60 | 0 | 40 | 0 | 95 | 40 |
| | 100 | 0 | 0 | 0 | 20 | 0 | 20 | 0 | 30 | 0 |
| | 30 | 0 | 0 | 0 | 0 | 0 | 0 | 0 | 0 | 0 |
| | 10 | 0 | 0 | 0 | 0 | 0 | 0 | 0 | 0 | 0 |

| Example no. | Rate g/ha | Weeds | | | | | | | | |
|---|---|---|---|---|---|---|---|---|---|---|
| | | SETFA | DATST | PANDI | SEBEX | SORVU | IPOSS | BRAPP | DIGSA | XANST |
| 1 | 900 | 100 | 20 | nd | 0 | 95 | 0 | nd | 100 | 0 |
| | 300 | 100 | 0 | nd | 0 | 80 | 0 | 70 | 100 | nd |
| | 100 | 40 | 0 | nd | 0 | 60 | 0 | 40 | 100 | nd |
| | 30 | 0 | 0 | nd | 0 | 0 | 0 | 0 | 60 | 0 |
| | 10 | 0 | 0 | nd | 0 | 0 | 0 | 0 | 0 | 0 |
| 15 | 900 | 100 | 0 | nd | 35 | 95 | 0 | 85 | 100 | 0 |
| | 300 | 70 | 0 | nd | 0 | 60 | 0 | 50 | 100 | 0 |
| | 100 | 99 | 0 | nd | 0 | 20 | 0 | 40 | 80 | 0 |
| | 30 | 0 | 0 | nd | 0 | 0 | 0 | 0 | 40 | 0 |
| | 10 | 0 | 0 | nd | 0 | 0 | 0 | 0 | 70 | 0 | nd = no data

TABLE 16

Percent inhibition of warm season crops and weeds (PPI application)

| Example no. | Rate g/ha | Crops | | | Weeds | | | | | |
|---|---|---|---|---|---|---|---|---|---|---|
| | | ZEAMX | GLYMX | ORYSA | ECHCG | ABUTH | PANMI | SOLNI | SORHA | AMARE |
| 1 | 900 | 70 | 40 | 90 | 100 | 80 | 100 | 100 | 100 | 100 |
| | 300 | 25 | 0 | 60 | 100 | 20 | 100 | 75 | 100 | 100 |
| | 100 | 0 | 0 | 40 | 99 | 0 | 99 | 0 | 100 | 80 |
| | 30 | 0 | 0 | 0 | 20 | 0 | 60 | 0 | 50 | 60 |
| | 10 | 0 | 0 | 0 | 0 | 0 | 0 | 0 | 70 | 0 |
| 2 | 900 | 80 | 20 | 30 | 100 | 75 | nd | 90 | 100 | 100 |
| | 300 | 50 | 10 | 0 | 100 | 20 | 100 | 100 | 100 | 100 |
| | 100 | 10 | 0 | 0 | 80 | 0 | 80 | 90 | 80 | 95 |
| | 30 | 5 | 0 | 0 | 40 | 0 | 20 | 30 | 70 | 100 |
| 3 | 900 | 55 | 15 | 70 | 100 | 60 | 100 | 100 | 100 | 100 |
| | 300 | 30 | 0 | 20 | 100 | 30 | 100 | 100 | 100 | 100 |
| | 100 | 10 | 0 | 0 | 99 | 0 | 100 | 100 | 100 | 100 |
| | 30 | 5 | 0 | 0 | 100 | 0 | 100 | 70 | 99 | 90 |
| 4 | 900 | 50 | 10 | 20 | 100 | 70 | 100 | 100 | 100 | 100 |
| | 300 | 40 | 0 | 0 | 100 | 20 | 100 | 100 | 100 | 100 |
| | 100 | 5 | 0 | 0 | 100 | 0 | 100 | 95 | 100 | 100 |
| | 30 | 0 | 0 | 0 | 20 | 0 | 0 | 60 | 60 | 70 |
| 8 | 900 | 95 | 65 | 70 | 100 | 100 | 100 | 100 | 100 | 100 |
| | 300 | 65 | 40 | 50 | 100 | 20 | 100 | 100 | 100 | 100 |
| | 100 | 5 | 10 | 40 | 100 | 10 | 100 | 100 | 90 | 100 |
| | 30 | 0 | 0 | 0 | 90 | 0 | 100 | 50 | 100 | 100 |
| 9 | 900 | 99 | 40 | 95 | 100 | 90 | 100 | 99 | 100 | 100 |
| | 300 | 90 | 20 | 70 | 100 | 60 | 100 | 100 | 100 | 100 |
| | 100 | 10 | 10 | 0 | 100 | 0 | 80 | 100 | 100 | 100 |
| | 30 | 0 | 0 | 0 | 90 | 0 | 60 | 95 | 100 | 90 |
| 10 | 900 | 40 | 70 | 0 | 100 | 50 | 100 | 100 | 100 | 100 |
| | 300 | 10 | 10 | 30 | 100 | 30 | 99 | 80 | 100 | 100 |
| | 100 | 0 | 0 | 0 | 50 | 0 | 80 | 100 | 50 | 40 |
| | 30 | 0 | 0 | 0 | 0 | 0 | 0 | 60 | 0 | 0 |
| | 10 | 0 | 0 | 0 | 0 | 0 | 0 | 20 | 0 | 0 |
| 11 | 900 | 10 | 30 | 40 | 99 | 20 | 100 | 100 | 100 | 100 |
| | 300 | 0 | 10 | 40 | 70 | 20 | 80 | 50 | 80 | 95 |
| | 100 | 0 | 0 | 0 | 40 | 0 | 20 | 30 | 30 | 40 |
| | 30 | 0 | 0 | 0 | 0 | 0 | 0 | 0 | 0 | 90 |
| | 10 | 0 | 0 | 0 | 0 | 0 | nd | 0 | 0 | 0 |

TABLE 16-continued

Percent inhibition of warm season crops and weeds (PPI application)

| | | | | | | | | | | |
|---|---|---|---|---|---|---|---|---|---|---|
| 13 | 900 | 50 | 70 | 80 | 100 | 85 | 100 | 100 | 100 | 100 |
| | 300 | 10 | 30 | 60 | 100 | 20 | 100 | 95 | 100 | 100 |
| | 100 | 5 | 0 | 70 | 100 | 0 | 70 | 60 | 90 | 70 |
| | 30 | 0 | 0 | 30 | 80 | 0 | 90 | 30 | 100 | 90 |
| | 10 | 0 | 0 | 0 | 10 | 0 | 100 | 0 | 30 | 0 |
| 15 | 900 | 85 | 65 | 0 | 90 | 40 | 100 | 99 | 95 | 100 |
| | 300 | 60 | 15 | 0 | 100 | 50 | 100 | 100 | 100 | 100 |
| | 100 | 20 | 0 | 0 | 90 | 20 | 99 | 20 | 100 | 80 |
| | 30 | 0 | 0 | 0 | 50 | 0 | 70 | 0 | 20 | 100 |
| | 10 | 0 | 0 | 0 | 10 | 0 | 10 | 0 | 40 | 20 |
| 16 | 900 | 80 | 80 | 100 | 100 | 95 | 100 | 100 | 100 | 100 |
| | 300 | 40 | 10 | 90 | 100 | 30 | 100 | 95 | 100 | 100 |
| | 100 | 20 | 10 | 30 | 100 | 0 | 100 | 100 | 100 | 100 |
| | 30 | 5 | 0 | 0 | 100 | 0 | 100 | nd | 70 | 100 |
| | 10 | 0 | 0 | 0 | 90 | 0 | 100 | 100 | 0 | 80 |
| 17 | 900 | 95 | 80 | 60 | 100 | 100 | 100 | 100 | 100 | 100 |
| | 300 | 30 | 20 | 30 | 100 | 40 | 100 | 70 | 100 | 100 |
| | 100 | 20 | 0 | 0 | 100 | 0 | 100 | 80 | 100 | 100 |
| | 30 | 0 | 0 | 0 | 95 | 0 | 100 | 0 | 60 | 95 |
| | 10 | 0 | 0 | 0 | 40 | 0 | 60 | 0 | 95 | 60 |
| 18 | 900 | 20 | 50 | 10 | 100 | 90 | 100 | 90 | 100 | 100 |
| | 300 | 15 | 0 | 15 | 100 | 70 | 100 | 99 | 100 | 100 |
| | 100 | 10 | 0 | 0 | 100 | 0 | 100 | 20 | 100 | 100 |
| | 30 | 0 | 0 | 0 | 100 | 0 | 40 | 0 | 100 | 100 |
| | 10 | 0 | 0 | 0 | 30 | 0 | 0 | 0 | 100 | 30 |
| 19 | 900 | 35 | 20 | 20 | 100 | 60 | 100 | 90 | 100 | 100 |
| | 300 | 10 | 0 | nd | 100 | 0 | 100 | 40 | 100 | 95 |
| | 100 | 10 | 0 | 0 | 100 | 0 | 100 | 0 | 100 | 95 |
| | 30 | 0 | 0 | 0 | 20 | 0 | 60 | 0 | 80 | 20 |
| | 10 | 0 | 0 | 0 | 20 | 0 | 0 | 0 | 60 | 0 |
| 20 | 900 | 40 | 30 | 40 | 100 | 80 | 100 | 100 | 80 | 100 |
| | 300 | 20 | 0 | 10 | 70 | 30 | 65 | 30 | 80 | 100 |
| | 100 | 0 | 0 | 0 | 20 | 0 | 100 | 0 | 20 | 50 |
| | 30 | 0 | 0 | 0 | 0 | 0 | 20 | 0 | 0 | 0 |
| | 10 | 0 | 0 | 0 | 0 | 0 | 0 | 0 | nd | 0 |

| Example | Rate | Weeds | | | | | | | | |
|---|---|---|---|---|---|---|---|---|---|---|
| no. | g/ha | SETFA | DATST | PANDI | SEBEX | SORVU | IPOSS | BRAPP | DIGSA | XANST | CHEAL |
| 1 | 900 | 100 | 95 | nd | 20 | 100 | 80 | 100 | 100 | 0 | nd |
| | 300 | 100 | 40 | nd | 0 | 100 | 60 | 90 | 100 | 0 | nd |
| | 100 | 100 | 0 | nd | 0 | 100 | nd | 100 | 100 | 0 | nd |
| | 30 | 70 | 0 | nd | 0 | 80 | nd | 0 | 95 | 0 | nd |
| | 10 | 100 | 0 | nd | 0 | 20 | 0 | 0 | 80 | 0 | nd |
| 2 | 900 | 90 | 70 | 100 | nd | 100 | 95 | 70 | 100 | 0 | 100 |
| | 300 | 100 | 80 | 100 | nd | 95 | 100 | 90 | 90 | 0 | 100 |
| | 100 | 100 | 10 | 100 | nd | 100 | 20 | 50 | 99 | 0 | 95 |
| | 30 | 20 | 0 | 100 | nd | 50 | nd | 80 | 85 | 0 | 90 |
| 3 | 900 | 100 | 100 | 100 | nd | 100 | 80 | 90 | 100 | 60 | 100 |
| | 300 | 100 | 70 | 100 | nd | 100 | 100 | 100 | 100 | 0 | 100 |
| | 100 | 100 | 30 | 100 | nd | 95 | 50 | 100 | 100 | 0 | 99 |
| | 30 | 100 | 0 | 80 | nd | 70 | 0 | 30 | 70 | 0 | 80 |
| 4 | 900 | 100 | 75 | 100 | nd | 100 | 100 | 100 | 100 | 40 | 100 |
| | 300 | 100 | 40 | 100 | nd | 100 | 60 | 100 | 100 | 0 | 100 |
| | 100 | 100 | 0 | 100 | nd | 45 | 80 | 60 | 90 | 0 | 100 |
| | 30 | 100 | 0 | 0 | nd | 0 | 0 | 0 | 85 | 0 | 60 |
| 8 | 900 | 100 | 100 | 100 | nd | 100 | 100 | 100 | 100 | 50 | 100 |
| | 300 | 100 | 100 | 100 | nd | 100 | 90 | 100 | 100 | 20 | 100 |
| | 100 | 100 | 60 | 100 | nd | 70 | 70 | 70 | 100 | 0 | 100 |
| | 30 | 90 | 30 | 95 | nd | 50 | 0 | 40 | 100 | 0 | 70 |
| 9 | 900 | 100 | 100 | 100 | nd | 100 | 100 | 100 | 100 | 60 | 100 |
| | 300 | 100 | 80 | 100 | nd | 100 | 40 | 100 | 100 | 30 | 100 |
| | 100 | 100 | 0 | 100 | nd | 70 | 100 | 80 | 100 | 0 | 100 |
| | 30 | 95 | 0 | 100 | nd | 60 | 0 | 70 | 95 | 0 | 95 |
| 10 | 900 | 100 | 100 | 100 | nd | 100 | 50 | 100 | 100 | 10 | 100 |
| | 300 | 100 | 20 | 100 | nd | 95 | 0 | 100 | 85 | 0 | 100 |
| | 100 | 80 | 0 | 100 | nd | 20 | 0 | 70 | 90 | 0 | 60 |
| | 30 | 60 | 0 | 50 | nd | 0 | 0 | 20 | 0 | 0 | 60 |
| | 10 | 0 | 0 | 0 | nd | 0 | 0 | 0 | 0 | 0 | 30 |
| 11 | 900 | 100 | 80 | 100 | nd | 100 | 0 | 100 | 100 | 0 | 100 |
| | 300 | 60 | 20 | 99 | nd | 65 | 0 | 100 | 90 | 0 | 100 |
| | 100 | 90 | 20 | 70 | nd | 10 | 0 | 60 | 70 | 0 | 60 |
| | 30 | 0 | 0 | 0 | nd | 0 | 0 | 0 | 0 | 0 | 60 |
| | 10 | 0 | 0 | 0 | nd | 0 | 0 | 0 | 0 | 0 | 30 |

TABLE 16-continued

Percent inhibition of warm season crops and weeds (PPI application)

| | | | | | | | | | | | |
|---|---|---|---|---|---|---|---|---|---|---|---|
| 13 | 900 | 100 | 100 | 100 | nd | 100 | 100 | 100 | 100 | 30 | 100 |
| | 300 | 100 | 90 | 100 | nd | 100 | 10 | 99 | 100 | 0 | 100 |
| | 100 | 90 | 50 | 90 | nd | 90 | 0 | 95 | 100 | 0 | 100 |
| | 30 | 99 | 30 | 100 | nd | 50 | 0 | 80 | 75 | 0 | 20 |
| | 10 | 0 | 0 | 40 | nd | 0 | 0 | 40 | 0 | 0 | 30 |
| 15 | 900 | 100 | 90 | nd | 50 | 100 | 20 | 100 | 100 | nd | nd |
| | 300 | 100 | 65 | nd | 0 | 100 | 20 | 99 | 100 | 0 | nd |
| | 100 | 99 | 0 | nd | nd | 100 | nd | 95 | 100 | 0 | nd |
| | 30 | 40 | 0 | nd | 0 | 60 | 0 | 0 | 70 | 0 | nd |
| | 10 | nd | 0 | nd | 0 | 10 | nd | 0 | 90 | 0 | nd |
| 16 | 900 | 100 | 100 | 100 | nd | 100 | 50 | 100 | 100 | 95 | 100 |
| | 300 | 100 | 70 | 100 | nd | 100 | 0 | 100 | 100 | 0 | 100 |
| | 100 | 100 | 20 | 100 | nd | 100 | 0 | 100 | 90 | 0 | 100 |
| | 30 | 80 | 0 | 100 | nd | 80 | 0 | 60 | 100 | 0 | 100 |
| | 10 | 80 | 0 | 0 | nd | 20 | 0 | 20 | 70 | 0 | 100 |
| 17 | 900 | 100 | 99 | nd | nd | 100 | nd | 100 | 100 | 100 | nd |
| | 300 | 100 | 60 | nd | nd | 100 | nd | 100 | 80 | 20 | nd |
| | 100 | 100 | 30 | nd | nd | 100 | nd | 50 | 80 | 0 | nd |
| | 30 | 100 | 0 | nd | nd | 70 | nd | 0 | 80 | 0 | nd |
| | 10 | 100 | 0 | nd | nd | 20 | nd | 0 | 60 | 0 | nd |
| 18 | 900 | 100 | 100 | nd | nd | 100 | nd | 100 | 100 | 30 | nd |
| | 300 | 100 | 60 | nd | nd | 100 | nd | 100 | 100 | 0 | nd |
| | 100 | 90 | 0 | nd | nd | 50 | nd | 0 | 80 | 0 | nd |
| | 30 | 90 | 0 | nd | nd | 50 | nd | 0 | 80 | 0 | nd |
| | 10 | 100 | 0 | nd | nd | 20 | nd | 0 | 20 | 0 | nd |
| 19 | 900 | 100 | 99 | nd | nd | 100 | nd | 100 | 99 | 90 | nd |
| | 300 | 100 | 90 | nd | nd | 100 | nd | 100 | 90 | 0 | nd |
| | 100 | 90 | 0 | nd | nd | 65 | nd | 30 | 90 | 0 | nd |
| | 30 | 100 | 0 | nd | nd | 50 | nd | 0 | 40 | 0 | nd |
| | 10 | 90 | 0 | nd | nd | 30 | nd | 0 | nd | 0 | nd |
| 20 | 900 | 100 | 60 | nd | nd | 100 | nd | 60 | 99 | 50 | nd |
| | 300 | 90 | 20 | nd | nd | 40 | nd | 30 | 100 | nd | nd |
| | 100 | 99 | 0 | nd | nd | 30 | nd | 0 | 90 | 0 | nd |
| | 30 | 70 | 0 | nd | nd | 0 | nd | 0 | 80 | 0 | nd |
| | 10 | 0 | 0 | nd | nd | 0 | nd | 0 | 0 | 0 | nd | nd = no data

TABLE 17

Percent inhibition of cool season crops and weeds (PPI application)

| Example | Rate | Crops | | | Weeds | | | | | | |
|---|---|---|---|---|---|---|---|---|---|---|---|
| no. | g/ha | TRZAW | HORVX | BRSNS | ALOMY | GALAP | SETVI | POLCO | LOLMG | SINAR | BROTE |
| 1 | 900 | 30 | 50 | 100 | 100 | 100 | 100 | 100 | 100 | 100 | 100 |
| | 300 | 10 | 30 | 99 | 100 | 100 | 100 | 100 | 100 | 100 | 50 |
| | 100 | 0 | 10 | 20 | 99 | 100 | 99 | 90 | 95 | 100 | 20 |
| | 30 | 0 | 0 | 60 | 80 | 70 | 80 | 30 | 95 | 100 | 0 |
| 2 | 900 | 30 | 100 | 100 | 100 | 100 | 100 | 100 | 100 | 100 | 100 |
| | 300 | 30 | 20 | 100 | 100 | 100 | 100 | 65 | 100 | 100 | 50 |
| | 100 | 0 | 30 | 80 | 90 | 100 | 40 | 40 | 99 | 100 | 40 |
| | 30 | 0 | 0 | 0 | 50 | 60 | 80 | 40 | 40 | 10 | 0 |
| 3 | 900 | 40 | 80 | 100 | 100 | 100 | 100 | 100 | 100 | 100 | 95 |
| | 300 | 20 | 10 | 100 | 99 | 100 | 100 | 90 | 100 | 100 | 90 |
| | 100 | 0 | 0 | 100 | 90 | 100 | 100 | 70 | 100 | 100 | 30 |
| | 30 | 0 | 0 | 100 | 60 | 100 | 100 | 60 | 40 | 100 | 0 |
| 4 | 900 | 45 | 90 | 100 | 100 | 100 | 100 | 100 | 100 | 100 | 90 |
| | 300 | 30 | 50 | 100 | 100 | 100 | 100 | 90 | 100 | 100 | 85 |
| | 100 | 10 | 0 | 100 | 95 | 100 | 100 | 60 | 100 | 100 | 50 |
| | 30 | 0 | 0 | 80 | 70 | 75 | 99 | 0 | 80 | 95 | 0 |
| 8 | 900 | 60 | 60 | 100 | 100 | 100 | 100 | 100 | 100 | 80 | 99 |
| | 300 | 20 | 10 | 40 | 100 | 100 | 100 | 85 | 100 | 100 | 65 |
| | 100 | 0 | 0 | 0 | 95 | 100 | 100 | 0 | 100 | 95 | 0 |
| | 30 | 0 | 0 | 0 | 0 | 0 | 100 | 0 | 35 | 100 | 0 |
| 9 | 900 | 70 | 40 | 100 | 100 | 100 | 100 | 100 | 100 | 100 | 95 |
| | 300 | 10 | 10 | 100 | 100 | 100 | 100 | 95 | 100 | 70 | 20 |
| | 100 | 0 | 0 | 95 | 95 | 70 | 100 | 0 | 100 | 100 | 0 |
| | 30 | 0 | 0 | 50 | 40 | 100 | 99 | 0 | 60 | 100 | 0 |
| 10 | 900 | 20 | 20 | 95 | 100 | 100 | 100 | 95 | 99 | 100 | 60 |
| | 300 | 10 | 0 | 50 | 95 | 50 | 100 | 80 | 100 | 80 | 35 |
| | 100 | 0 | 0 | 0 | 100 | 80 | 90 | 60 | 65 | 100 | 10 |
| | 30 | 0 | 0 | 0 | 50 | 0 | 0 | 0 | 0 | 90 | 0 |
| | 10 | 0 | 0 | 0 | 0 | 0 | nd | 0 | 0 | 0 | 0 |

TABLE 17-continued

Percent inhibition of cool season crops and weeds (PPI application)

| | | | | | | | | | | | |
|---|---|---|---|---|---|---|---|---|---|---|---|
| 11 | 900 | 20 | 10 | 0 | 100 | 90 | 100 | 30 | 95 | 99 | 20 |
| | 300 | 0 | 0 | 0 | 45 | 20 | 95 | 0 | 99 | 0 | 0 |
| | 100 | 0 | 0 | 0 | 20 | 0 | 99 | 0 | 70 | 0 | 0 |
| | 30 | 0 | 0 | 0 | 0 | 0 | 90 | 0 | 40 | 0 | 0 |
| | 10 | 0 | 0 | 0 | 0 | 0 | 80 | 0 | 20 | 0 | 0 |
| 13 | 900 | 30 | 40 | 30 | 100 | 100 | 100 | 90 | 100 | 100 | 85 |
| | 300 | 20 | 10 | 70 | 99 | 40 | 100 | 80 | 100 | nd | 20 |
| | 100 | 20 | 20 | 0 | 99 | 0 | 100 | 40 | 70 | 100 | 10 |
| | 30 | 0 | 0 | 0 | 90 | 30 | 95 | 50 | 60 | 100 | 0 |
| | 10 | 0 | 0 | 0 | 40 | 0 | 30 | 0 | 20 | 70 | 0 |
| 16 | 900 | 20 | 20 | 75 | 100 | 100 | 100 | 95 | 100 | 100 | 90 |
| | 300 | 10 | 25 | 30 | 100 | 100 | 100 | 0 | 95 | 100 | 40 |
| | 100 | 10 | 10 | 0 | 100 | 100 | 95 | 0 | 90 | 100 | 35 |
| | 30 | 0 | 0 | 0 | 95 | 20 | 80 | 0 | 35 | 50 | 0 |
| | 10 | 0 | 0 | 0 | 40 | 0 | 100 | 0 | 45 | 0 | 0 |
| 17 | 900 | 60 | 60 | 95 | 100 | 100 | 100 | nd | 100 | 100 | 95 |
| | 300 | 30 | 30 | 60 | 90 | 80 | 100 | nd | 100 | 100 | 30 |
| | 100 | 10 | 10 | 0 | 100 | 40 | 70 | nd | 95 | 90 | 20 |
| | 30 | 0 | 0 | 0 | 60 | 60 | 70 | nd | 60 | 70 | 0 |
| | 10 | 0 | 0 | 0 | 50 | 0 | 40 | nd | 45 | 70 | 0 |
| 18 | 900 | 60 | 60 | 100 | 80 | 100 | 100 | nd | 100 | 100 | 90 |
| | 300 | 30 | 10 | 20 | 80 | 100 | 60 | nd | 100 | 100 | 20 |
| | 100 | 0 | 0 | nd | 30 | 70 | 100 | nd | 50 | 80 | 0 |
| | 30 | 0 | 0 | 0 | 60 | 60 | 100 | nd | 60 | 100 | 0 |
| | 10 | 0 | 0 | 0 | 60 | 70 | 100 | nd | 20 | 100 | 0 |
| 19 | 900 | 60 | 45 | 95 | 100 | 100 | 100 | nd | 100 | 100 | 95 |
| | 300 | 70 | 20 | 60 | 100 | 50 | 100 | nd | 100 | 100 | 60 |
| | 100 | 30 | 20 | 0 | 70 | 100 | 100 | nd | 100 | 100 | 20 |
| | 30 | 0 | 0 | 0 | 50 | 100 | 60 | nd | 70 | nd | 20 |
| | 10 | 0 | 0 | 0 | 60 | 85 | 50 | nd | 30 | 100 | 0 |
| 20 | 900 | 60 | 30 | 95 | 100 | 100 | 100 | nd | 75 | 70 | 50 |
| | 300 | 40 | 10 | 60 | 50 | 90 | 100 | nd | 85 | 60 | 40 |
| | 100 | 0 | 0 | 20 | 20 | 50 | 40 | nd | 60 | 80 | 0 |
| | 30 | 0 | 0 | 20 | 0 | 0 | 70 | nd | 30 | 80 | 0 |
| | 10 | 0 | 0 | 0 | 0 | 0 | 0 | nd | 0 | 30 | 0 |

| Example no. | Rate g/ha | Weeds | | | | | | | | |
|---|---|---|---|---|---|---|---|---|---|---|
| | | KCHSC | AVEFA | VERPE | POAAN | SASKR | AGSST | STEME | AGRRE | LAMPU | AEGCY |
| 1 | 900 | nd | 90 | nd | 100 | 100 | 100 | 95 | 95 | 100 | 60 |
| | 300 | nd | 95 | nd | 100 | 100 | 100 | 99 | 60 | 95 | 40 |
| | 100 | nd | 20 | nd | 99 | 100 | 100 | 100 | 20 | 70 | 0 |
| | 30 | nd | 0 | nd | 90 | 80 | 100 | 60 | 0 | 80 | 0 |
| 2 | 900 | nd | 50 | nd | 100 | 100 | 100 | 95 | 60 | 100 | 70 |
| | 300 | nd | 20 | nd | 100 | 85 | 100 | 80 | 30 | 95 | 20 |
| | 100 | nd | 10 | nd | 100 | 80 | 99 | 90 | 0 | 70 | 20 |
| | 30 | nd | 0 | nd | 80 | 50 | 100 | 60 | 0 | 30 | 0 |
| 3 | 900 | nd | 80 | nd | 100 | 100 | 100 | 100 | 95 | 100 | 90 |
| | 300 | nd | 100 | nd | 100 | 100 | 100 | 100 | 80 | 100 | 40 |
| | 100 | nd | 40 | nd | 100 | 80 | 100 | 80 | 50 | 95 | 50 |
| | 30 | nd | 20 | nd | 70 | 80 | 100 | 60 | 20 | 60 | 0 |
| 4 | 900 | nd | 100 | nd | 100 | 100 | 100 | 95 | 90 | 90 | 30 |
| | 300 | nd | 50 | nd | 100 | 99 | 100 | 80 | 80 | 80 | 50 |
| | 100 | nd | 10 | nd | 75 | 90 | 100 | 60 | 70 | 80 | 30 |
| | 30 | nd | 10 | nd | 95 | 75 | 100 | 10 | 50 | 40 | 0 |
| 8 | 900 | nd | 100 | nd | 100 | 100 | 100 | 99 | 100 | 100 | 20 |
| | 300 | nd | 95 | nd | 100 | 90 | 100 | 95 | 70 | 90 | 40 |
| | 100 | nd | 75 | nd | 100 | 50 | 100 | 80 | 40 | 100 | 50 |
| | 30 | nd | 10 | nd | 100 | 0 | 100 | 80 | 0 | 80 | 0 |
| 9 | 900 | nd | 100 | nd | 100 | 100 | 100 | 100 | 100 | 95 | 40 |
| | 300 | nd | 100 | nd | 100 | 95 | 100 | 80 | 80 | 100 | 30 |
| | 100 | nd | 20 | nd | 100 | 100 | 100 | 95 | 70 | 40 | 20 |
| | 30 | nd | 0 | nd | 90 | 50 | 99 | 70 | 0 | 0 | 0 |
| 10 | 900 | nd | 95 | 100 | 100 | 100 | 100 | 90 | 50 | 50 | 20 |
| | 300 | nd | 40 | 100 | 100 | 100 | 100 | 0 | 0 | 0 | 30 |
| | 100 | nd | 20 | 100 | 95 | 90 | 100 | 0 | 0 | nd | 20 |
| | 30 | nd | 0 | 90 | 10 | 20 | 70 | 0 | 0 | 0 | 0 |
| | 10 | nd | 0 | 70 | 0 | 10 | 90 | 0 | 0 | 0 | 0 |
| 11 | 900 | nd | 60 | 100 | 70 | 65 | 100 | 30 | 0 | 0 | 10 |
| | 300 | nd | 0 | 100 | 0 | 30 | 90 | 0 | 0 | 0 | 0 |
| | 100 | nd | 0 | 100 | 0 | nd | 60 | 0 | 0 | 0 | 0 |
| | 30 | nd | 0 | 90 | 0 | 20 | 50 | 0 | 0 | 0 | 0 |
| | 10 | nd | 0 | 90 | 0 | 0 | 60 | 0 | 0 | 0 | 0 |

TABLE 17-continued

Percent inhibition of cool season crops and weeds (PPI application)

| | | | | | | | | | | | |
|---|---|---|---|---|---|---|---|---|---|---|---|
| 13 | 900 | nd | 90 | 100 | 95 | 100 | 100 | 99 | 60 | 90 | 40 |
|  | 300 | nd | 50 | 100 | 100 | 100 | 100 | 100 | 40 | 0 | 60 |
|  | 100 | nd | 0 | 100 | 90 | 80 | 100 | 20 | 20 | 0 | 0 |
|  | 30 | nd | 0 | 100 | 50 | 30 | 95 | 0 | 0 | nd | 0 |
|  | 10 | nd | 0 | 75 | 0 | 20 | 60 | 0 | 0 | 0 | 0 |
| 16 | 900 | nd | 90 | 100 | 100 | 100 | 100 | 95 | 70 | 90 | 60 |
|  | 300 | nd | 80 | 100 | 100 | 80 | 100 | 60 | 20 | 80 | 20 |
|  | 100 | nd | 0 | 100 | 65 | 80 | 100 | 60 | 0 | 90 | 0 |
|  | 30 | nd | 0 | 95 | 50 | 90 | 100 | 75 | 0 | 80 | 0 |
|  | 10 | nd | 0 | 100 | 20 | 65 | 100 | 40 | 0 | 50 | 0 |
| 17 | 900 | 100 | 100 | 100 | 100 | 100 | 100 | nd | 70 | 100 | 40 |
|  | 300 | 100 | 75 | 90 | 95 | 60 | 100 | nd | 60 | 100 | 20 |
|  | 100 | 100 | 50 | 0 | 70 | 0 | 95 | nd | 50 | 100 | 0 |
|  | 30 | 100 | 15 | 0 | 60 | 0 | 95 | nd | 40 | 100 | 0 |
|  | 10 | 70 | 0 | 0 | 10 | 0 | 70 | nd | 0 | 100 | 0 |
| 18 | 900 | 100 | 99 | 99 | 100 | 100 | 100 | nd | 80 | 70 | 10 |
|  | 300 | 100 | 50 | 95 | 80 | 80 | 99 | nd | 20 | 0 | 20 |
|  | 100 | 80 | 10 | 80 | 65 | 80 | 100 | nd | 20 | nd | 0 |
|  | 30 | 80 | 0 | 20 | 50 | 0 | 60 | nd | 30 | 0 | 0 |
|  | 10 | 40 | 0 | 0 | 20 | 0 | 100 | nd | 0 | 0 | 0 |
| 19 | 900 | 100 | 60 | 99 | 100 | 95 | 100 | nd | 80 | 99 | 20 |
|  | 300 | 80 | 70 | 20 | 100 | 60 | 90 | nd | 20 | 0 | 50 |
|  | 100 | 80 | 30 | 20 | 10 | 0 | 100 | nd | 10 | nd | 20 |
|  | 30 | 20 | 0 | 40 | 0 | 0 | 90 | nd | 0 | 0 | 0 |
|  | 10 | 0 | 0 | 0 | 0 | 0 | 60 | nd | 0 | 0 | 0 |
| 20 | 900 | 100 | 60 | 95 | 99 | 100 | 100 | nd | 80 | 95 | 0 |
|  | 300 | 100 | 0 | 90 | 90 | 0 | 75 | nd | 40 | 100 | 0 |
|  | 100 | 100 | 0 | 50 | 60 | 40 | 85 | nd | 65 | 80 | 0 |
|  | 30 | 50 | 0 | 90 | 30 | 0 | 10 | nd | 10 | 60 | 0 |
|  | 10 | 50 | 0 | 0 | 0 | 0 | 0 | nd | 0 | 90 | 0 | nd = no data

As can be seen from the data in Tables 16 and 17 above, some of the compounds of the invention appear to be quite safe on certain crops and can thus be used for selective control of weeds in these crops.

Formulations

The herbicidal compositions of this invention, including concentrate formulations which require dilution prior to application, contain at least one herbicidal active ingredient as provided herein and optionally at least one adjuvant in liquid or solid form. Such compositions are prepared by admixing the active ingredient with one or more adjuvants including solvents, diluents, extenders, carriers, and conditioning agents such as wetting agents, emulsifying agents and dispersing agents, to provide finely divided particulate solids, granules, pellets, solutions, or dispersions such as suspensions or emulsions. Thus, it is believed that a herbicidal compound of the invention could be used with an adjuvant such as for example a finely divided solid, an organic liquid, water, a wetting agent, a dispersing agent, an emulsifying agent or any suitable combination of these.

Wetting agents and emulsifying agents useful in compositions of the invention are surfactants, without restriction as to type or chemical class. Nonionic, anionic, cationic and amphoteric types, or combinations of more than one of these types, are all useful in particular situations. The term "alkyl" as conventionally understood in the surfactant art, and as used in the present context, refers to one or more $C_{8-22}$ linear or branched, saturated or unsaturated aliphatic hydrocarbyl moieties. The term "aryl" encompasses a wide range of aromatic moieties including for example phenyl, benzene, toluene, xylene and naphthalene groups.

Hydrophobic moieties of surfactants useful in compositions of the invention can be essentially hydrocarbon based. Alternatively, the hydrophobic moieties can contain silicon atoms, for example in the form of siloxane groups such as heptamethyltrisiloxane groups, or fluorine atoms, for example as partially-fluorinated alkyl or perfluoroalkyl chains.

Many surfactants useful herein have a chemical structure that comprises one or more moieties each consisting of a single $C_{2-4}$ alkylene oxide unit or a polymerized or copolymerized chain of $C_{2-4}$ alkylene oxide units. Such surfactants are referred to as polyoxyalkylene surfactants and include nonionic, anionic, cationic and amphoteric types. Polyoxyalkylene surfactants useful in presently contemplated compositions contain about 2 to about 100 $C_{2-4}$ alkylene oxide units.

Anionic surfactants include alkyl and alkylaryl carboxylates, alkyl and alkylaryl polyoxyalkylene ether carboxylates, alkyl and alkylaryl sulfates and sulfonates, alkyl and alkylaryl polyoxyalkylene ether sulfates and sulfonates, naphthalene sulfonates and formaldehyde condensates thereof, petroleum sulfonates, sulfonated vegetable oils, sulfosuccinate and semisulfosuccinate esters, sulfosuccinamates, isethionates, taurates, sarcosinates, alkyl and alkylaryl phosphates, and alkyl and alkylaryl polyoxyalkylene phosphates.

Nonionic surfactants include polyoxyethylene alkyl and alkylaryl ethers, such as polyoxyethylene primary and secondary alcohols, polyoxyethylene alkylphenols and polyoxyethylene acetylenic diols, polyoxyethylene alkyl esters, such as ethoxylated fatty acids, polyoxyethylene polyoxypropylene block copolymers, polyoxyethylene sorbitan alkyl esters, glyceryl alkyl esters, sucrose esters, and alkyl polyglycosides.

Cationic surfactants include polyoxyethylene tertiary alkylamines and alkenylamines, such as polyoxyethylene fatty amines, quaternary ammonium surfactants and polyoxyethylene alkyletheramines, imidazolines and pyridines.

Amphoteric surfactants, encompassing as is customary in the art surfactants more correctly described as zwitterionic, include polyoxyethylene alkylamine oxides, alkylbetaines, phosphatidylcholines, phosphatidylethanolamines, and alkyl-substituted amino acids.

Standard reference sources from which one of skill in the art can select suitable surfactants, without limitation to the above mentioned classes, include *Handbook of Industrial Surfactants,* Second Edition (1997) published by Gower, *McCutcheon's Emulsifiers and Detergents,* North American and International Editions (1997) published by MC Publishing Company, and *International Cosmetic Ingredient Dictionary,* Sixth Edition (1995) Volumes 1 and 2, published by the Cosmetic, Toiletry and Fragrance Association.

Dispersing agents useful in compositions of the invention include methyl cellulose, polyvinyl alcohol, sodium lignin sulfonates, polymeric alkyl naphthalene sulfonates, sodium naphthalene sulfonate, and polymethylene bisnaphthalene sulfonate.

Compounds of the invention can be formulated for practical use as any suitable liquid or solid formulation type, including without restriction an emulsifiable concentrate, emulsifiable gel, water-in-oil emulsion, oil-in-water emulsion, water-in-oil-in-water (multiple) emulsion, microemulsion, suspension concentrate, suspoemulsion, wettable powder, emulsifiable granule, water-dispersible granule, dust, granule, tablet or briquette.

In an emulsifiable concentrate, a compound of the invention is dissolved in a suitable organic solvent that is itself normally of low solubility in, or miscibility with, water. Also included is a system of one or more emulsifying agents selected to promote rapid and acceptably stable emulsification when the concentrate is diluted in water prior to application. Alternatively but more rarely, the concentrate can be diluted in an organic liquid such as kerosene for application. Emulsifiable concentrates are liquid, but if desired they can be processed to form an emulsifiable gel by methods known in the art. Suitable organic solvents for a compound of the invention illustratively include N,N-dimethylformamide, dimethylsulfoxide (DMSO), N-methylpyrrolidone, hydrocarbons, and water-immiscible ethers, esters and ketones.

An illustrative emulsifiable concentrate formulation of the invention has the following composition, all amounts of ingredients being expressed as percent by weight.

| | |
|---|---|
| Compound of Example 1 | 11.6% |
| Solvent: Aromatic 200 (Exxon) + γ-butyrolactone, 4:1 | 78.4% |
| Emulsifying agent Armul ™ 1496 (Stepan) | 5.0% |
| Emulsifying agent Armul ™ 1505 (Stepan) | 5.0% |

Emulsions (whether water-in-oil or oil-in-water) comprise an aqueous phase and an oil phase. Typically a compound of the invention is dissolved in an organic solvent of low solubility in water, to form the oil phase. The aqueous phase can optionally contain a water-soluble active ingredient such as a glyphosate salt. The oil phase can be continuous (water-in-oil) or discontinuous (oil-in-water); in either case the emulsion is stabilized by means of a system of one or more emulsifying agents. In preparing a water-in-oil-in-water emulsion, a water-in-oil emulsion is first prepared having a compound of the invention in the oil phase, together with a first emulsifying system as described immediately above. This water-in-oil emulsion is then itself dispersed in an aqueous medium using a second emulsifying system. Either the internal or the external aqueous phase so formed, or both such phases, can optionally contain a water-soluble active ingredient.

In a suspension concentrate, a compound of the invention is present in the form of a fine particulate solid, dispersed with the aid of dispersing agents in a liquid, preferably aqueous, medium to form a stable suspension. A suspoemulsion has both a discontinuous oil phase emulsified in an aqueous medium and a discontinuous solid particulate phase dispersed in the same aqueous medium; a compound of the invention can be present in either the oil phase or the particulate phase. A second water-insoluble active ingredient can optionally be present in the same or the other discontinuous phase. In both suspension concentrates and suspoemulsions, a water-soluble active ingredient such as a salt of glyphosate can optionally be present in the aqueous phase.

An illustrative suspension concentrate formulation of the invention has the following composition, all amounts of ingredients being expressed in grams per liter (g/l).

| | |
|---|---|
| Compound of Example 1 | 206.4 g/l |
| Propylene glycol | 40.0 g/l |
| Atlox ™ 4913 (ICI) | 20.0 g/l |
| Atlox ™ 4896 (ICI) | 10.0 g/l |
| Rhodorsil ™ 432R (Rhône-Poulenc) | 1.0 g/l |
| Rhodopol ™ 23 (Rhône-Poulenc) | 2.0 g/l |
| Phylatol (Coalite) | 2.0 g/l |
| Demineralized water | 805.5 g/l |

Liquid concentrate formulations of the invention, such as the types mentioned immediately above, contain about 0.1% to about 60%, preferably about 5% to about 50%, by weight of a compound of the invention. In the case of an emulsifiable concentrate, the upper limit is determined by the solubility limit of the compound in the selected solvent. In the case of an emulsion or suspension concentrate, the upper limit is determined primarily by the limit of colloidal stability of the composition.

Wettable powders are water-dispersible fine particulate solid compositions comprising a compound of the invention, typically with an inert solid extender and one or more wetting and/or dispersing agents. The extender is usually of mineral origin such as for example a natural clay, diatomaceous earth, or a synthetic mineral derived from silica. Illustrative examples of such extenders include kaolinite, attapulgite clay and synthetic magnesium silicate. Wettable powder compositions of the invention usually contain about 0.5% to about 60%, preferably about 5% to about 20%, by weight of a compound of the invention, about 0.25% to about 25%, preferably about 1% to about 15%, by weight of wetting agent(s), about 0.25% to about 25%, preferably about 1% to about 15%, by weight of dispersing agent(s), and about 5% to about 95%, preferably about 5% to about 50%, by weight of an inert solid extender. Where required, about 0.1% to about 2% by weight of the composition can be comprised of a corrosion inhibitor or anti-foaming agent or both.

Water-dispersible granule formulations of the invention have similar ingredients to the wettable powders just mentioned, but in such formulations the fine solid particles are agglomerated to form larger aggregates that are less dusty and more convenient to handle. Any of a variety of granulation techniques known in the art can be used in preparing such formulations, including without restriction spray drying, pan granulation, extrusion granulation and fluid bed agglomeration. The extrusion process described in United Kingdom Patent Application No. 1 433 882 is one illustrative process that can be useful in preparing granular compositions of the present invention.

Dry formulations for direct application to soil without dilution in water include dusts and granules. Granules of the invention are physically stable particulate compositions comprising a compound of the invention adsorbed on or distributed through a matrix formed of an inert, finely-divided particulate extender. In order to aid leaching of the compound of the invention from the granules, a surfactant can be present in the composition. Natural clays, pyrophyllites, illite and vermiculite are examples of operable classes of particulate mineral extenders. Preferred extenders are porous, adsorptive, preformed particulates such as preformed and screened particulate attapulgite; heat-expanded, particulate vermiculite; or finely divided clays including kaolin, hydrated attapulgite or bentonite.

Granular compositions of the invention typically contain about 0.1 to about 30 parts by weight of a compound of the invention and 0 to about 5 parts by weight of surfactant per 100 parts by weight of extender.

Compositions of the invention can also contain other ingredients, for example fertilizers, other herbicides, other pesticides, safeners, etc. Among herbicides that can be formulated together with a compound of the invention are acetochlor, acifluorfen, aclonifen, alachlor, ametryn, amidosulfuron, anilofos, asulam, atrazine, azafenidin, azimsulfuron, benazolin, benfluralin, benfuresate, bensulfuron-methyl, bensulide, bentazon, benzofenap, bialaphos, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D, daimuron, dalapon, 2,4-DB, desmedipham, desmetryn, dicamba, dichlobenil, dichlorprop, diclofop-methyl, diflufenican, dimefuron, dimepiperate, dimethachlor, dimethametryn, dimethenamid, dinitramine, dinoterb, diphenamid, diquat, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, fenoxaprop, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fluroxypyr, fomesafen, fosamine, glufosinate, halosulfuron, haloxyfop-methyl, hexazinone, imazameth, imazamethabenz, imazamox, imazapic, imazapyr, imazaquin, imazethapyr, imazosulfuron, indanofan, isoproturon, isouron, isoxaben, isoxaflutole, isoxapyrifop, lactofen, lenacil, linuron, MCPA, MCPB, mecoprop, mefenacet, metamitron, metazachlor, methabenzthiazuron, methylarsonic acid, methyldymron, metobenzuron, metobromuron, metolachlor, metosulam, metoxuron, metribuzin, metsulfuron, molinate, monolinuron, naproanilide, napropamide, naptalam, neburon, nicosulfuron, nonanoic acid, norflurazon, orbencarb, oryzalin, oxadiargyl, oxadiazon, oxasulfuron, oxyfluorfen, paraquat, pebulate, pendimethalin, pentanochlor, pentoxazone, phenmedipham, picloram, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfamic acid, sulfentrazone, sulfometuron, sulfosulfuron, 2,3,6-TBA, TCA, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, triclopyr, trietazine, trifluralin, triflusulfuron and vemolate.

Herbicides useful in combination with a compound of the invention can be selected from those listed in standard reference works such as *The Pesticide Manual*, 11th Edition, British Crop Protection Council (1997), and *Farm Chemicals Handbook* '97, Meister Publishing Company (1997).

Fertilizers useful in combination with a compound of the invention include ammonium nitrate, urea, potash and superphosphate fertilizers. Other useful additives include materials in which plant organisms take root and grow such as compost, manure, humus, sand etc.

Application

In accordance with the present invention, a herbicidally effective amount of a compound of the invention is applied to soil containing seeds or vegetative propagules of a plant species to be killed or controlled. The compound can be applied to the soil surface or can be incorporated into the soil in any convenient fashion. The application of liquid and particulate solid compositions of the invention to soil can be carried out by conventional methods, e.g., by spraying with a hydraulic sprayer or spinning disk applicator, by dusting or by use of a granule applicator. Application can be made by hand-carried, backpack or ground-travelling equipment. Compounds of the invention are also suitable for application from airplanes as a dust or spray because of their effectiveness at low dosages.

The exact amount of active ingredient to be employed is dependent on various factors, including plant species and stage of development thereof, type and condition of soil, amount of rainfall and the specific compound employed. In selective pre-emergence application to soil, a dosage of about 0.02 to about 11.2 kg/ha, preferably from about 0.1 to about 5.60 kg/ha, is usually employed. Lower or higher rates may be useful in some instances. One skilled in the art can readily determine from this specification, including the above examples, and by routine experimentation a suitable rate to be applied in any particular case.

The term "soil" is employed herein in its broadest sense to be inclusive of all conventional "soils" as defined in Webster's New International Dictionary, Second Edition, Unabridged (1961). Thus, the term refers to any substance or medium in which vegetation may take root and grow, and includes not only earth but also compost, manure, muck, humus, sand, etc. adapted to support plant growth.

While illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as including all features which would be treated as equivalents thereof by those skilled in the art to which the invention pertains.

What is claimed is:

1. A compound having the formula

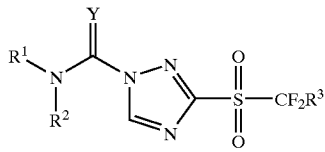

wherein:

Y is oxygen or sulfur;

$R^1$ and $R^2$ are independently
$C_{1-6}$ alkyl, $C_{2-4}$ alkenyl, $C_{2-4}$ alkynyl, $C_{3-6}$ cycloalyl, $C_{5-6}$ cycloalkenyl, $C_{6-10}$ aryl, $(C_{1-3})$alkyl$(C_{3-6})$cycloalkyl, $(C_{2-3})$alkenyl$(C_{3-6})$cycloalkyl, $(C_{2-3})$alkyny$(C_{3-6})$cycloalkyl, halo$(C_{1-6})$alkyl, halo$(C_{2-4})$alkenyl, halo$(C_{2-4})$alkynyl, halo$(C_{3-6})$cycloalkyl, $(C_{1-4})$alkoxy$(C_{1-6})$alkyl, $(C_{1-4})$alkoxy$(C_{2-4})$alkenyl, $(C_{1-4})$alkoxy$(C_{2-4})$alkynyl, $(C_{1-4})$alkoxy$(C_{3-6})$cycloalkyl,
halo$(C_{1-4})$alkoxy$(C_{1-6})$alkyl, halo$(C_{1-4})$alkoxy$(C_{2-4})$alkenyl, halo$(C_{1-4})$alkoxy$(C_{2-4})$alkynyl, halo$(C_{1-4})$alkoxy$(C_{3-6})$cycloalkyl,
$(C_{6-10})$aryl$(C_{1-4})$alkyl, $(C_{3-6})$cycloalkyl$(C_{1-4})$alkyl, $(C_{5-6})$cycloalkenyl$(C_{1-4})$alkyl, $(C_{1-4})$alkyl$(C_{3-6})$cycloalkyl$(C_{1-4})$alkyl, $(C_{1-4})$alkyl$(C_{5-6})$cycloalkenyl$(C_{1-4})$alkyl, $(C_{2-4})$alkenyl$(C_{3-6})$cycloalkyl$(C_{1-4})$alkyl, $(C_{2-4})$alkynyl$(C_{5-6})$cycloalkyl$(C_{1-4})$akyl,
halo$(C_{3-6})$cycloalkyl$(C_{1-4})$alkyl or $(C_{1-4})$alkoxy$(C_{3-6})$cycloalkyl$(C_{1-4})$alkyl groups; or $R^1$ and $R^2$ together represent a ring-forming group that is (a) a $C_{4-5}$ alkylene group or (b) a $(C_{1-2})$alkylenyloxy$(C_{2-3})$alkylene group having up to four carbon atoms, such that said ring-forming group (a) or (b) and the carbamoyl nitrogen atom to which it is attached form a nitrogen-containing five or six membered ring; said ring-forming group being optionally substituted with one or two substituents each independently selected from the group consisting of $C_{1-4}$ alkyl, $C_{2-4}$ alkenyl, $C_{2-4}$ alkynyl, $C_{3-6}$ cycloalkyl, $C_{1-4}$ alkoxy, halo and halo$(C_{1-4})$alkoxy; and $R^3$ is a hydrogen, halogen, $C_{1-8}$ alkyl, halo$(C_{1-4})$alkyl, $C_{1-4}$ alkoxy, $(C_{1-4})$alkoxy$(C_{1-4})$alkyl, $C_{3-6}$ cycloalkyl, halo$(C_{3-6})$cycloalkyl, $C_{2-4}$ alkenyl, $(C_{3-6})$cycloalkyl$(C_{2-4})$alkenyl, $(C_{1-4})$alkoxy$(C_{2-4})$alkenyl, halo$(C_{2-4})$alkenyl, $(C_{3-6})$cycloalkenyl, halo$(C_{3-6})$cycloalkenyl, tri$(C_{1-4})$alkylsilyl$(C_{1-4})$alkyl, $(C_{1-4})$alkylthio, $(C_{6-10})$aryl$(C_{1-4})$alkylthio, $C_{6-10}$ aryl or $(C_{6-10})$aryl$(C_{1-4})$alkyl group, wherein each of said $C_{6-10}$ aryl, $(C_{6-10})$aryl$(C_{1-4})$alkyl or $(C_{6-10})$aryl$(C_{1-4})$alkylthio groups is unsubstituted or substituted on the aryl ring with one to three substituents each independently selected from $C_{1-6}$ alkyl, $C_{2-4}$ alkenyl, $C_{2-4}$ alkynyl, $C_{3-6}$ cycloalkyl, halo, halo$(C_{1-4})$alkyl, $C_{1-4}$ alkoxy, halo$(C_{1-4})$alkoxy, cyano, nitro, $(C_{1-6})$alkoxycarbonyl, $(C_{1-4})$alkylthio and halo$(C_{1-4})$alkylthio groups;

or an agronomically acceptable acid addition salt or metal complex of such compound.

2. A compound of claim 1 wherein $R^3$ is a hydrogen, halogen, $C_{1-8}$ alkyl, halo$(C_{1-4})$alkyl, $C_{3-6}$ cycloalkyl, halo$(C_{3-6})$cycloalkyl, $C_{2-4}$ alkenyl, $(C_{3-6})$cycloalkyl$(C_{2-4})$alkenyl, $(C_{1-4})$alkoxy$(C_{2-4})$alkenyl, halo$(C_{2-4})$alkenyl, $C_{3-6}$ cycloalkenyl, halo$(C_{3-6})$cycloalkenyl, $C_{6-10}$ aryl or $(C_{6-10})$aryl$(C_{1-6})$alkyl group, wherein said $C_{6-10}$ aryl or $(C_{6-10})$aryl$(C_{1-6})$alkyl groups are unsubstituted or substituted on the aryl ring with one to three substituents each independently selected from $C_{1-6}$ alkyl, $C_{2-4}$ alkenyl, $C_{2-4}$ alkynyl, $C_{3-6}$ cycloalkyl, halo, halo$(C_{1-4})$alkyl, $C_{1-4}$ alkoxy, halo$(C_{1-4})$alkoxy, cyano, nitro, $(C_{1-6})$alkoxycarbonyl, $(C_{1-4})$alkylthio and halo$(C_{1-4})$alkylthio groups.

3. A compound of claim 1 wherein $R^1$ and $R^2$ are each ethyl groups.

4. A compound of claim 3 wherein $R^3$ is a hydrogen, halogen, halo$(C_{1-4})$alkyl or $(C_{1-4})$alkylthio group.

5. A compound of claim 3 wherein $R^3$ is selected from bromo, difluoromethyl and ethylthio groups.

6. A composition for use as a selective herbicide comprising a herbicidally effective amount of a compound of claim 1 and an agronomically acceptable carrier.

7. A method of selectively controlling weeds in a crop comprising treating plants or soil with a herbicidally effective amount of a compound of claim 1.

* * * * *

UNITED STATES PATENT AND TRADEMARK OFFICE
CERTIFICATE OF CORRECTION

PATENT NO.     : 6,461,997 B1
DATED          : October 8, 2002
INVENTOR(S)    : Shridhar G. Hegde and Martin D. Mahoney It is certified that error appears in the above-identified patent and that said Letters Patent is hereby corrected as shown below:

<u>Title page,</u>
Item [57], ABSTRACT, replace "$C_{1-4}$" first occurrence with -- $C_{1-14}$ --.

<u>Column 49,</u>
Line 14, replace "cycloalyl" with -- cycloalkyl --.
Line 17, replace "alkyny($C_{3-6}$)cycloalkyl" with -- alkynyl($C_{3-6}$)cycloalkyl --.
Line 28, replace "($C_{2-4}$)alkynyl($C_{5-6}$)cycloalkyl($C_{1-4}$)akyl" with
-- ($C_{2-4}$)alkynyl($C_{5-6}$)cycloalkyl($C_{1-4}$)alkyl --.

Signed and Sealed this

Seventeenth Day of December, 2002

JAMES E. ROGAN
*Director of the United States Patent and Trademark Office*